(12) United States Patent
Ross et al.

(10) Patent No.: US 10,130,391 B2
(45) Date of Patent: Nov. 20, 2018

(54) EXTERNAL FIXATION STRUTS

(71) Applicant: TEXAS SCOTTISH RITE HOSPITAL FOR CHILDREN, Dallas, TX (US)

(72) Inventors: John David Ross, Ovilla, TX (US); Mikhail L. Samchukov, Coppell, TX (US); Alexander M. Cherkashin, Flower Mound, TX (US); John G. Birch, Dallas, TX (US)

(73) Assignee: Texas Scottish Rite Hospital For Children, Dallas, TX (US)

( * ) Notice: Subject to any disclaimer, the term of this patent is extended or adjusted under 35 U.S.C. 154(b) by 0 days.

(21) Appl. No.: 15/611,670

(22) Filed: Jun. 1, 2017

(65) Prior Publication Data

US 2017/0265898 A1 Sep. 21, 2017

Related U.S. Application Data

(62) Division of application No. 15/014,706, filed on Feb. 3, 2016, now Pat. No. 9,717,530.

(51) Int. Cl.
*A61B 17/66* (2006.01)
*A61B 17/62* (2006.01)
(Continued)

(52) U.S. Cl.
CPC .............. *A61B 17/66* (2013.01); *A61B 17/62* (2013.01); *A61B 17/645* (2013.01); *A61B 17/6491* (2013.01); *A61B 2017/606* (2013.01)

(58) Field of Classification Search
CPC ......... A61B 17/66; A61B 17/60; A61B 17/62; A61B 17/64; A61B 17/645;
(Continued)

(56) References Cited

U.S. PATENT DOCUMENTS 5,314,426 A 5/1994 Pohl et al.
5,429,638 A 7/1995 Muschler et al.
(Continued)

FOREIGN PATENT DOCUMENTS

| EP | 2085037 A1 | 5/2009 |
|---|---|---|
| WO | 2009/018349 A2 | 2/2009 |
| WO | 2009/102904 A1 | 8/2009 |

OTHER PUBLICATIONS

Kristiansen, Leif Pal, Thesis: Biomechanics Laboratory, Department of Orthopaedics, Rikshospitalet, University of Oslo, Norway, "Reconstructive surgery of the human tibia by use of external ring fixator and the Ilizarov method," (2009), Acta Orthopaedica Supplementum, No. 331, vol. 80, 48 pages.

(Continued)

*Primary Examiner* — Pedro Philogene
(74) *Attorney, Agent, or Firm* — Baker & McKenzie LLP

(57) ABSTRACT

Dynamization struts and methods of use are provided. A dynamization strut may comprise a sleeve, a shaft, a biasing member, and a bushing. The sleeve may comprise an inner recess with a first and second section. The shaft may comprise an interior section to be disposed within the inner recess of the sleeve. The biasing member may be disposed around the interior section of the shaft, and sized to fit within the first section of the inner recess of the sleeve. The bushing may be secured against a portion of the shaft. Rotation of the bushing may provide for compressive movement of the biasing member relative to the sleeve and shaft. Compression of the biasing member may occur without a corresponding change in a total length of the dynamization strut. Rather, changes in the length of the strut may occur as a result of external compressive forces acting upon it.

13 Claims, 14 Drawing Sheets

(51) Int. Cl.
*A61B 17/64* (2006.01)
*A61B 17/60* (2006.01)

(58) Field of Classification Search
CPC ............ A61B 17/6458; A61B 17/6491; A61B 2017/606; A61B 2017/564; A61B 2017/00398; A61B 2017/00017; A61B 2017/00137; A61B 2017/00132
USPC .................. 606/54–60, 62–68, 246–289
See application file for complete search history.

(56) References Cited

U.S. PATENT DOCUMENTS

| | | | |
|---|---|---|---|
| 5,451,225 A | 9/1995 | Ross, Jr. et al. | |
| 5,626,579 A | 5/1997 | Muschler et al. | |
| 5,863,292 A | 1/1999 | Tosic | |
| 5,871,484 A | 2/1999 | Spievack et al. | |
| 5,928,230 A | 7/1999 | Tosic | |
| 5,935,127 A | 8/1999 | Border | |
| 8,057,474 B2 | 11/2011 | Knuchel et al. | |
| 8,162,984 B2 | 4/2012 | Weirich et al. | |
| 8,172,885 B2 | 5/2012 | Songer et al. | |
| 8,197,490 B2 * | 6/2012 | Pool | A61B 17/7004 606/90 |
| 8,221,467 B2 | 7/2012 | Butler et al. | |
| 8,444,644 B2 * | 5/2013 | Ross | A61B 17/62 606/56 |
| 8,506,566 B2 * | 8/2013 | Karidis | A61B 17/66 606/57 |
| 8,574,232 B1 | 11/2013 | Ross et al. | |
| 8,679,117 B2 | 3/2014 | Knuchel et al. | |
| 9,078,700 B2 | 7/2015 | Ross et al. | |
| 9,949,758 B2 * | 4/2018 | Vikinsky | A61B 17/62 |
| 2002/0165500 A1 | 11/2002 | Bechtold et al. | |
| 2005/0143735 A1 | 6/2005 | Kyle | |
| 2007/0118122 A1 | 5/2007 | Butler et al. | |
| 2007/0173837 A1 | 7/2007 | Chan et al. | |
| 2012/0209269 A1 | 8/2012 | Pool et al. | |
| 2013/0023876 A1 | 1/2013 | Rabiner et al. | |

OTHER PUBLICATIONS

International Search Report and Written Opinion, PCT/US2015/026719, dated Jun. 30, 2015, 12 pages.

* cited by examiner

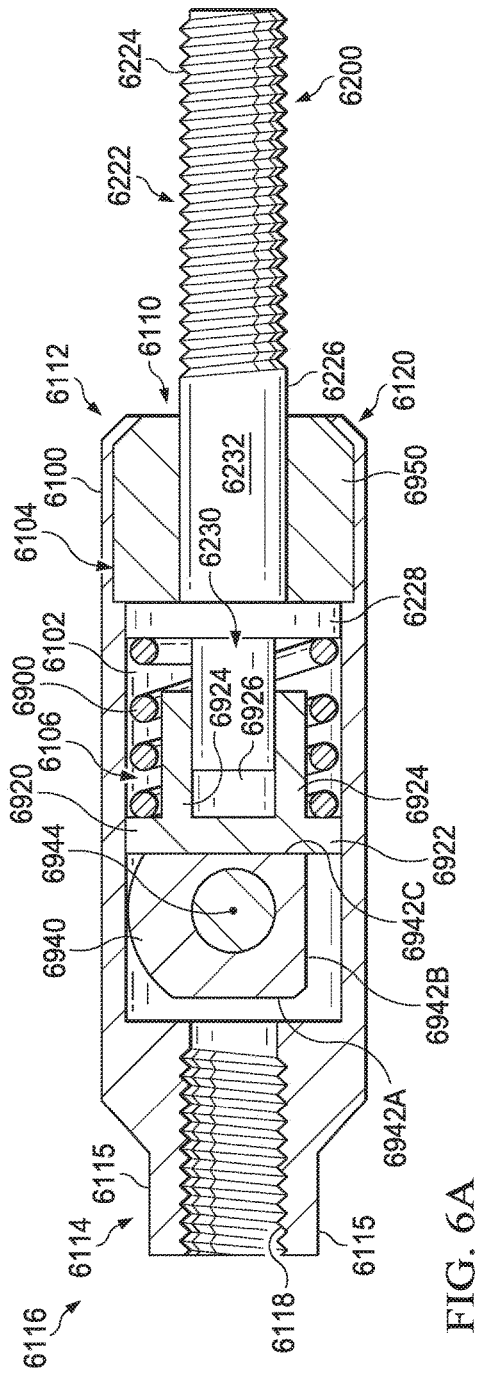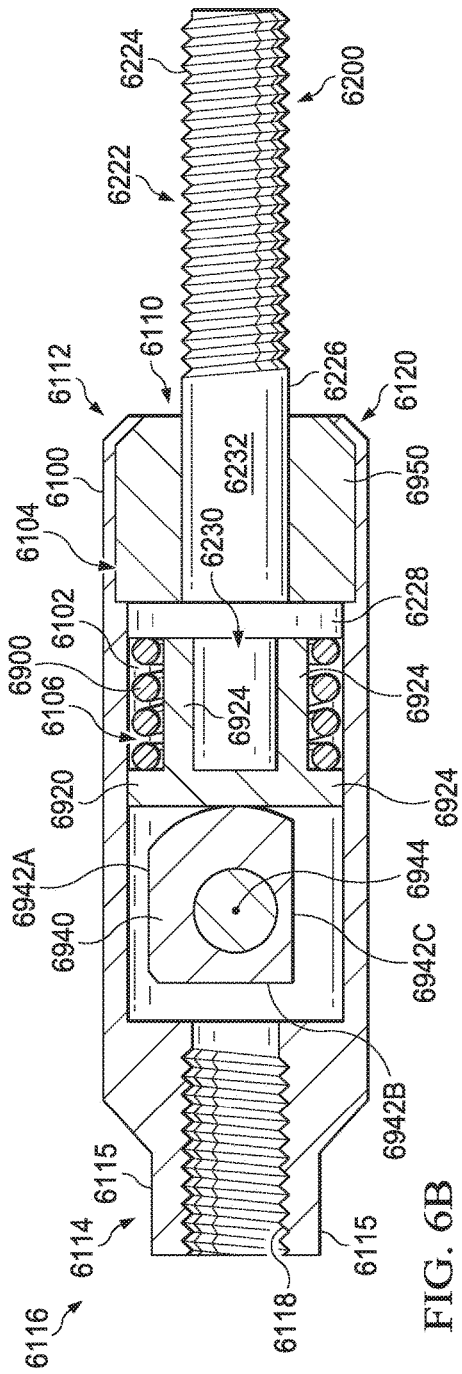
FIG. 6A
FIG. 6B

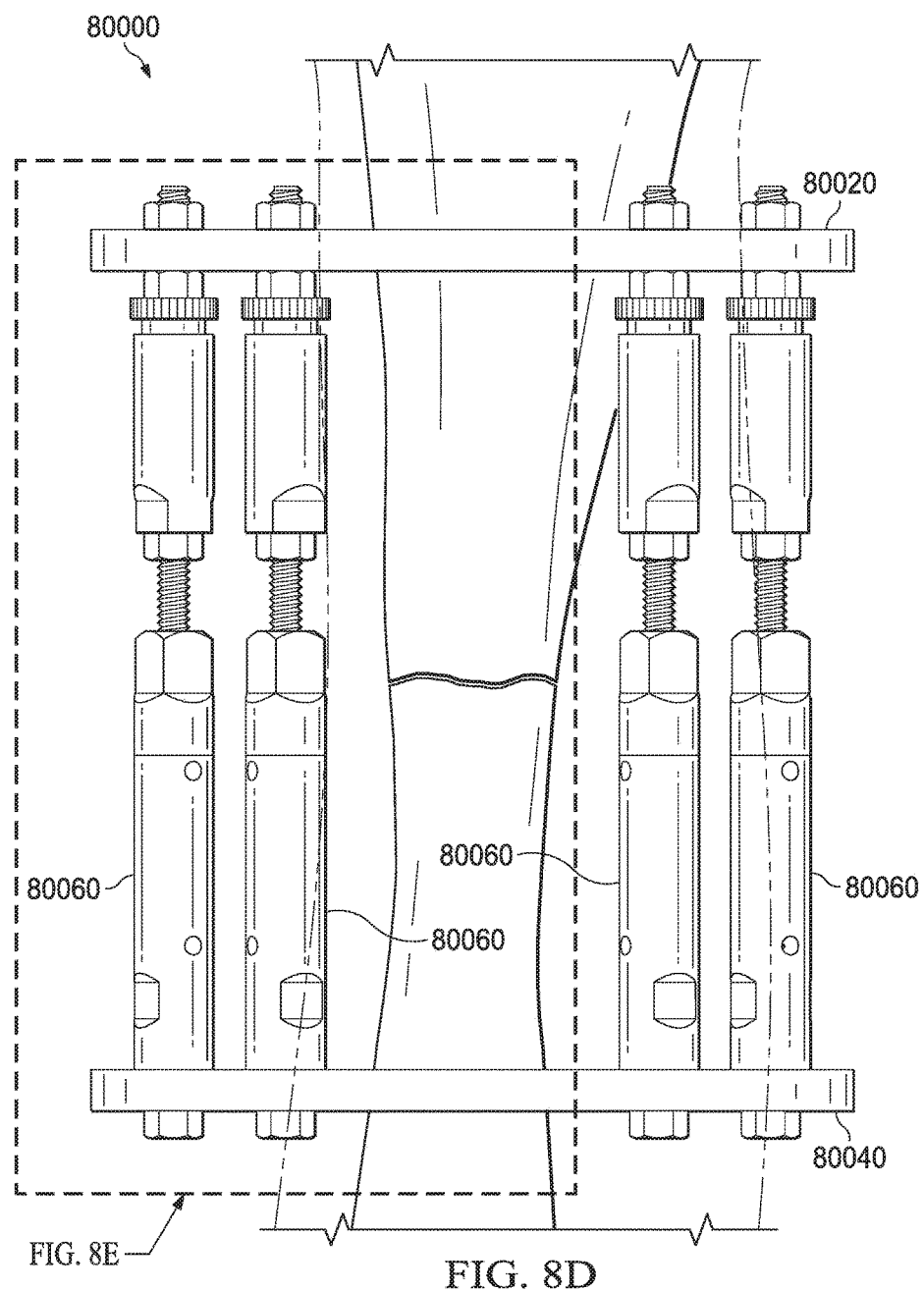

EXTERNAL FIXATION STRUTS

CROSS REFERENCE TO RELATED APPLICATIONS

This application is a divisional of, and claims priority to, U.S. patent application Ser. No. 15/014,706, filed on Feb. 3, 2016 and entitled, "External Fixation Struts," the entirety of which is hereby incorporated by reference for all purposes.

FIELD OF THE DISCLOSURE

The present disclosure relates in general to the field of external fixation connection rods and struts. More specifically, external fixation connection rods and struts of the present disclosure may provide for dynamization of corresponding external fixation devices.

BACKGROUND OF THE DISCLOSURE

Without limiting the scope of the disclosure, this background is described in connection with external fixation devices and specifically connection struts and rods. Generally, external fixation devices are commonly used in a variety of surgical procedures including limb lengthening, deformity correction, fracture reduction, and treatment of non-unions, mal-unions, and bone defects. The process involves a rigid framework comprising several rings that are placed externally around the limb and attached to bone segments using wires and half pins, which are inserted into the bone segments and connected to the related section of the external rigid framework. The opposite rings of the rigid framework are interconnected by either threaded or telescopic rods directly or in conjunction with uni-planar or multi-planar hinges, which allow the surgeon to connect opposite rings that are not parallel to each other after manipulation with bone segments either rapidly (acutely) or gradually over a period of time.

For example, in bone fracture reduction or non-union treatment, the wires and half pins are inserted into each bone segment and attached to rings of a rigid framework. The rigid framework is used to acutely reduce a displacement and restore alignment between the bone segments. During the realignment of the bone segments, the orientations of opposite rings are often not parallel. Those opposite rings of the rigid framework are connected together by threaded or telescopic rods with attached uni-planar or multi-planar hinges. This allows the opposite bone segment to be rigidly fixed until complete fracture healing or bone consolidation is completed.

Also for example, in limb lengthening, the bone is surgically divided into two segments and wires and half pins are inserted into bone segments above and below the surgical bone cut and attached to rings of a rigid framework interconnected by struts or telescopic connection rods. The rigid framework is used to gradually push the two bone segments apart longitudinally over a period of time (e.g., one millimeter a day), which allows the bone to gradually form in the gap between bone segments created by this distraction technique. Once the desired amount of lengthening is achieved (e.g., 5-6 cm), the external apparatus is stabilized into a fixed position and left on the bone segments until mineralization of the newly formed bone is complete (e.g., 3-6 months, depending on the nature of pathology and amount of lengthening).

Similarly, in deformity correction, the bone is surgically divided (usually at the apex of the deformity) into two segments, and wires and half pins are inserted into bone segments above and below the surgical bone cut and attached to rings of a rigid framework. Opposite rings of the rigid framework are connected together by threaded rods with attached uni-planar or multi-planar hinges and an angular distractor is used to gradually push the two bone segments apart angularly over a period of time.

For various bone treatments, introducing controlled destabilization can accelerate bone healing and significantly improve the strength of the fracture callus. Gradually increasing a load is an important part of the bone healing process. To achieve such controlled destabilization, the external fixation devices can be dynamized. There are many ways of achieving dynamization, examples including, for a unilateral fixator, removing its bars, sliding the bars further away from the bone, removing its pins, and/or releasing tension or compression from the system, and for a circular frame, removing its wires, releasing tension from the wires, removing its connection rods between rings, removing the rings from a ring block, and/or releasing tension or compression from the system. These techniques can be problematic since they often result in wide variations in the level of instability and may not effectively limit the dynamization to a desired direction or axis of movement.

SUMMARY

The present disclosure relates in general to the field of external fixation connection rods and struts. More specifically, external fixation connection rods and struts of the present disclosure may provide for dynamization of corresponding external fixation devices.

In some embodiments, a dynamization strut may comprise a sleeve, a shaft, a biasing member, a bushing, a holding pin, and a biasing pin. The sleeve may comprise an inner recess comprising a first section and a second section, wherein a diameter of the first section is larger than a diameter of the second section. The sleeve may also comprise a holding pin hole. The shaft may comprise an interior section disposed at least partially within the inner recess of the sleeve, and wherein the interior section comprises an annular indentation. The shaft may further comprise a first threaded section; a second threaded section, wherein the second threaded section comprises a larger diameter than the first threaded section, and wherein the second threaded section is adjacent to the interior section at one end and adjacent to the first threaded section at an opposing end; a biasing pin longitudinal slot disposed within the interior section; and a holding pin longitudinal slot disposed within the interior section, wherein the holding pin hole is configured to partially align with the holding pin longitudinal slot. The biasing member may be disposed around the interior section of the shaft, and may be sized to fit within the first section of the inner recess of the sleeve. The bushing may comprise an annular lip, wherein the annular lip has a diameter at least as large as the diameter of the first section of the inner recess of the sleeve. The bushing may also comprise a primary section, wherein the primary section is sized to be received into the first section of the inner recess of the sleeve. The bushing may also comprise a plurality of internal threads, wherein the internal threads are configured to mate with the second threaded section of the shaft. The holding pin may be inserted into the holding pin hole and the holding pin longitudinal slot. The biasing pin may be inserted into the biasing pin longitudinal slot. Rotation of the bushing may advantageously provide for compressive movement of the biasing member relative to the sleeve and shaft. Compression of the biasing member may be provided without a corresponding change in a total length of the external fixation strut. Thus, while the amount of dynamization provided by the external fixation strut may be adjusted, the total length of the external fixation strut may remain unchanged. Thus, any change in the length of the strut may occur as a result of external compressive forces acting upon it.

In some embodiments, the dynamization strut may further comprise a Teflon™ O-ring disposed within the annular indentation of the interior section of the shaft. The dynamization strut may further comprise a nut secured on the first threaded section of the shaft. In some embodiments, the sleeve may further comprise a plurality of internal threads disposed at one end of the sleeve configured to be secured to an external fixation device. In some embodiments, the biasing member may be a spring. The spring may have a spring constant of about 3.50 pounds/mm to about 4 pounds/mm. In some embodiments, one full rotation of the bushing along the second threaded section of the shaft may provide for a compressive movement of the biasing member of about 1 mm.

The holding pin longitudinal slot may have a length of about 3.5 mm to about 7 mm. The holding pin hole and the holding pin may both have diameters of about 3.2 mm. The biasing pin longitudinal slot may have a length of about 3.5 mm to about 7 mm. The biasing pin may have a diameter of about 3.2 mm. The sleeve may have a length of about 35 mm to about 50 mm. The shaft may have a length of about 30 mm to about 45 mm. The dynamization strut may provide for a dynamization range of about 3 mm.

According to another aspect of the present disclosure, a dynamization strut may comprise a sleeve, a shaft, a contact feature, a biasing member, and a rotatable feature. In some embodiments, a sleeve may comprise an inner recess comprising a first section and a second section, wherein a diameter of the first section is larger than a diameter of the second section. The shaft may comprise an interior section disposed at least partially within the inner recess of the sleeve, and wherein the interior section comprises an annular protrusion. The shaft may also comprise a threaded section. The contact feature may be disposed within the inner recess of the sleeve, wherein the contact feature comprises an annular protrusion and a longitudinal segment. The biasing member may be disposed within the inner recess of the sleeve and may be disposed between the annular protrusion of the contact feature and the annular protrusion of the shaft. The rotatable feature may comprise a plurality of surfaces. Rotation of the rotatable feature may result in a different one of the plurality of surfaces contacting the annular protrusion of the contact feature. Rotation of the bushing may advantageously provide for compressive movement of the biasing member relative to the sleeve and the shaft. Compression of the biasing member may be provided without a corresponding change in a total length of the external fixation strut. Thus, while the amount of dynamization provided by the external fixation strut may be adjusted, the total length of the external fixation strut may remain unchanged. Any change in the length of the strut may occur as a result of external compressive forces acting upon it.

In some embodiments, the plurality of surfaces of the rotatable feature may comprise four flat surfaces. Each of the four flat surfaces may have a different distance from a center of the rotatable feature. The different distances from the center of the rotatable feature may comprise 3.35 mm, 4.35 mm, and 5.35 mm. Rotation of the rotatable feature may result in compression or expansion of a spring within the inner recess of the sleeve. Rotation of the rotatable feature may result in movement of the contact feature within the inner recess of the sleeve. The longitudinal segment of the contact feature may be in contact with the annular protrusion of the shaft when the spring is fully compressed. The dynamization strut may further comprise an interior component disposed within the first section of the sleeve. In some embodiments, an end of the first section of the sleeve may comprise a narrowed section. The narrowed section may be in contact with the interior component and may secure the interior component within the first section of the sleeve.

In some embodiments, the sleeve may further comprise a plurality of internal threads disposed at one end of the sleeve. The plurality of internal threads of the sleeve may be configured to secure to an external fixation device.

In some embodiments, the biasing member may be a spring. The spring may have a spring constant of about 3.50 pounds/mm to about 4 pounds/mm. The sleeve may have a length of about 35 mm to about 50 mm. The shaft may have a length of about 30 mm to about 45 mm.

BRIEF DESCRIPTION OF THE DRAWINGS

Some embodiments of the disclosure may be understood by referring, in part, to the present disclosure and the accompanying drawings, wherein:

FIG. 6A illustrates an external fixation strut according to a specific example embodiment of the disclosure;

FIG. 6B illustrates an external fixation strut according to a specific example embodiment of the disclosure;

FIG. 8D illustrates an example embodiment of an external fixation device surrounding a person's bone with a fracture.

DETAILED DESCRIPTION

The present disclosure relates in general to the field of external fixation rods and struts. More specifically, external fixation struts of the present disclosure may provide for dynamization of corresponding external fixation devices. Embodiments of the present disclosure may advantageously provide for varying degrees of compressive movement of a biasing member of an external fixation strut relative to a shaft and a sleeve of the external fixation strut. Such features may advantageously provide for different degrees or amounts of dynamization in a corresponding external fixation device.

Figure 1:
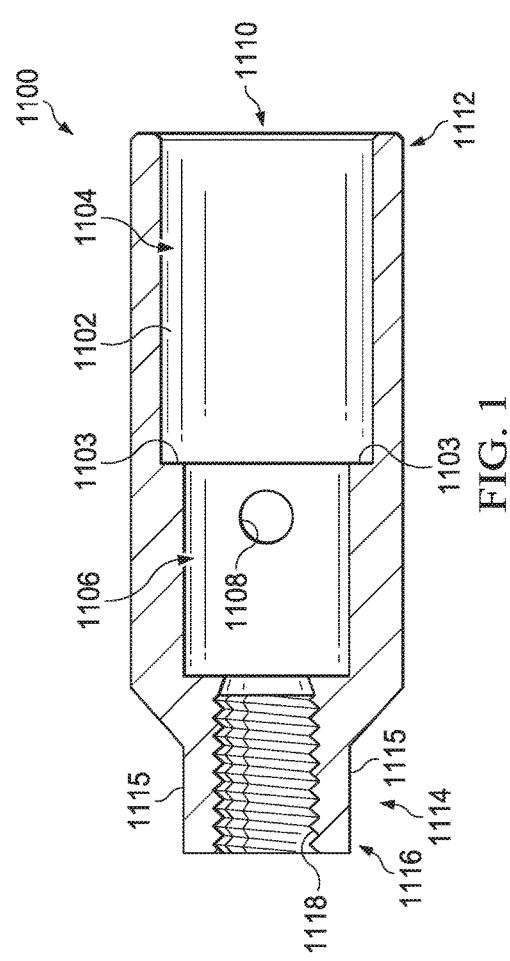
FIG. 1 illustrates a sleeve according to a specific example embodiment of the disclosure.

An external fixation strut according to embodiments of the present disclosure may comprise various components. FIG. 1 depicts a sleeve 1100 of an external fixation strut according to an embodiment of the present disclosure. As seen in FIG. 1, sleeve 1100 may comprise a substantially cylindrical geometry. Sleeve 1100 may comprise an inner recess 1102. The inner recess 1102 may provide for an opening 1110 at a first end 1112 of the sleeve 1100. Thus, other components of an external fixation strut may be received into the inner recess 1102 through the opening 1110.

The inner recess 1102 may further comprise a first section 1104 and a second section 1106. The first section 1104 may have a diameter that is larger than a diameter of the second section 1106. As a result, features that may fit into or otherwise be secured within the first section 1104 may not be able to enter or pass into the second section. Further, inner recess 1102 may comprise shoulder 1103. Other components, such as a biasing member, disposed within the first section 1104 may bias against shoulder 1103. The inner recess 1102 may have a length of about 30 mm to about 35 mm. In some embodiments, the inner recess 1102 may have a length of about 31.6 mm. The first section 1104 of the inner recess 1102 may have a length of about 15 mm to about 25 mm. In some embodiments, the first section 1104 of the inner recess 1102 may have a length about 19.3 mm. In some embodiments, the first section 1104 may have a diameter of about 12.7 mm to about 14.3 mm. The second section 1106 of the inner recess 1102 may have a length of about 10 mm to about 15 mm. In some embodiments, the second section 1106 of the inner recess 1102 may have a length about 12.3 mm. In some embodiments, the second section 1106 may have a diameter of about 9.5 mm to about 11.1 mm.

The sleeve 1100 of an external fixation strut may further comprise a holding pin hole 1108. The holding pin hole 1108 may be positioned along the sleeve 1100 in such a manner so that it runs through the second section 1106 of the inner recess 1102. The holding pin hole 1108 may provide for two corresponding holes on either side of the sleeve 1100. The holding pin hole 1108 may have a diameter of about 3 mm to about 4 mm. In some embodiments, the holding pin hole 1108 may have a diameter of about 3.18 mm.

The sleeve 1100 of an external fixation strut may further comprise a narrowed section 1114 at a second end 1116 of the sleeve 1100. The second end 1116 may be opposite to the previously discussed first end 1112 where the opening 1110 to the inner recess 1102 is disposed. A plurality of internal threads 1118 may be disposed at the second end 1116 of the sleeve 1100. The plurality of internal threads 1118 may allow an external fixation strut to be secured to an external fixation device. For example, an external fixation strut may be secured to a support structure. A support structure may comprise a plurality of rings. An external fixation strut may be secured directly to the support structure, or an external fixation strut may be secured to a threaded rod, which in turn is secured to the support structure. The plurality of internal threads 1118 may span a length of about 8 mm to about 12 mm. In some embodiments, the plurality of internal threads 1118 may span a length of about 9 mm.

The sleeve 1100 may have a diameter of about 15.9 mm to about 17.5 mm or about 15 mm to about 17 mm, and a length of about 35 mm to about 50 mm. In some embodiments, the sleeve 1100 may have a length of about 42 mm. The narrowed section 1114 of the sleeve 1100 may have a width of about 10 mm to about 13 mm, and a length of about 8 mm to about 12 mm. The narrowed section 1114 may have a length of about 9.5 mm. In some embodiments, sleeve 1100 may further comprise indented surfaces 1115 at the narrowed section 1114. The indented surfaces 1115 may provide contact points for a wrench to be secured against the sleeve 1100 so rotation or other manipulation may be facilitated. Narrowed section 1114 may comprise, for example, two to six indented surfaces 1115. Indented surfaces 1115 may comprise a length of about 6 mm.

Figure 2:
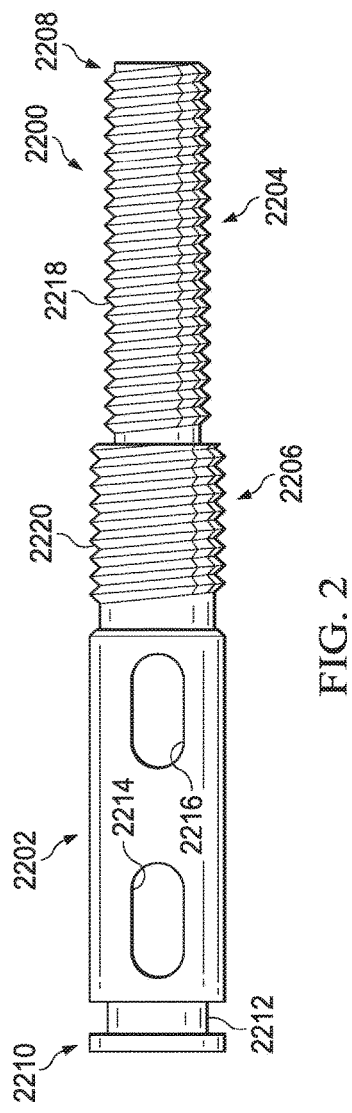
FIG. 2 illustrates a shaft according to a specific example embodiment of the disclosure.

An external fixation strut according to embodiments of the present disclosure may further comprise a shaft. FIG. 2 depicts a shaft 2200 of an external fixation strut according to an embodiment of the present disclosure. The shaft 2200 may comprise an interior section 2202, which may be sized and/or configured to be disposed at least partially within the inner recess 1102 of the sleeve 1100. The interior section 2202 may have a diameter that is smaller than both a diameter of the second section 1106 of the inner recess 1102 and a diameter of the first section 1104 of the inner recess 1102. Thus, the interior section 2202 of the shaft 2200 may be received into both the first section 1104 and the second section 1106 of the sleeve 1100 through the opening 1110 of the sleeve 1100. The interior section 2202 may have a length of about 20 mm to about 28 mm. In some embodiments, the interior section 2202 may have a length of about 24.5 mm. The interior section 2202 may have a diameter of about 6 mm to about 9 mm. In some embodiments, the interior section 2202 may have a diameter of about 7.94 mm.

The shaft 2200 may comprise a first threaded section 2204 and a second threaded section 2206 at a first end 2208 of the shaft 2200. The first threaded section 2204 may have first external threads 2218 thereon; and the second threaded section 2206 may have second external threads 2220 thereon. The second threaded section 2206 may be adjacent to the first threaded section 2204 at one end of the second threaded section 2206, and adjacent to the interior section 2202 at an opposite end of the second threaded section 2206. In some embodiments, the second threaded section 2206 may comprise a larger diameter than the first threaded section 2204. The first threaded section 2204 may have a length of about 15 mm to about 25 mm; the second threaded section 2206 may have a length of about 8 mm to about 15 mm. In some embodiments, the first threaded section 2204 may have a length of about 22 mm, and the second threaded section 2206 may have a length of about 11 mm. The first threaded section 2204 may have a diameter of about 6 mm to about 8 mm; the second threaded section 2206 may have a diameter of about 6 mm to about 8 mm.

In some embodiments, the first threaded section 2204 and the second threaded section 2206 may have differing diameters and differing threading dimensions. Such embodiments advantageously prevent features secured on the first threaded section 2204 from advancing into the second threaded section 2206, or vice versa. In some embodiments, the first threaded section 2204 and the second threaded section 2206 may have the same diameters and the same threading dimensions. Such embodiments may advantageously provide for greater ease of manufacturing the components of an external fixation strut. However, such embodiments may require that certain features threaded against the first threaded section 2204 or the second threaded section 2206 be secured into a particular position.

The shaft 2200 of an external fixation strut may further comprise an annular indentation 2212 within the interior section 2202. The annular indentation 2212 may be disposed near a second end 2210 of the shaft 2200. The annular indentation 2212 may run along the circumference of the interior section 2202, and may comprise and indentation of about 2 mm to about 2.5 mm.

The shaft 2200 of an external fixation strut may further comprise a holding pin longitudinal slot 2214. The holding pin longitudinal slot 2214 may be positioned along the shaft 2200 in such a manner so that it runs through the interior section 2202 of the shaft 2200. The holding pin longitudinal slot 2214 may provide for two corresponding slots on either side of the interior section 2202 of the shaft 2200. The holding pin longitudinal slot 2214 may have a length of about 3.5 mm to about 7 mm, and may be sized so that the holding pin hole 1108 may at least partially align with the holding pin longitudinal slot 2214.

The shaft 2200 of an external fixation strut may further comprise a biasing pin longitudinal slot 2216. The biasing pin longitudinal slot 2216 may be positioned along the shaft 2200 in such a manner so that is runs through the interior section 2202 of the shaft 2200. The biasing pin longitudinal slot 2216 may provide for two corresponding slots on either side of the interior section 2202 of the shaft 2200. The biasing pin longitudinal slot 2216 may have a length of about 3.5 mm to about 7 mm. The biasing pin longitudinal slot 2216 may be disposed closer to the first end 2208 of the shaft 2200, whereas the holding pin longitudinal slot 2214 may be disposed closer to the second end 2210 of the shaft 2200.

Figure 3A:
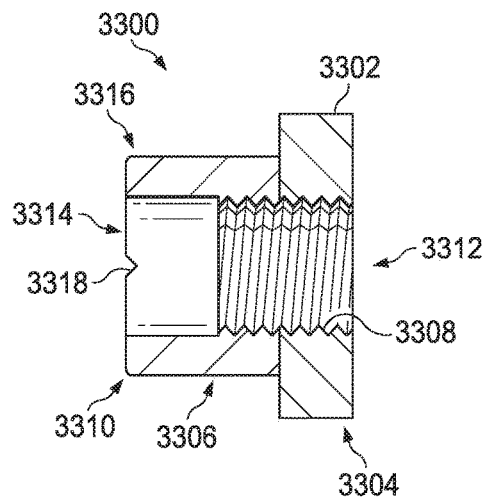
FIG. 3A illustrates a bushing according to a specific example embodiment of the disclosure.
Figure 3B:
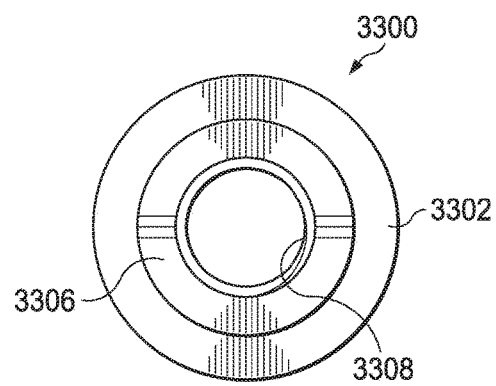
FIG. 3B illustrates a bushing according to a specific example embodiment of the disclosure.

An external fixation strut according to embodiments of the present disclosure may further comprise a bushing. FIG. 3A and FIG. 3B depict a bushing 3300 of an external fixation strut according to an embodiment of the present disclosure. As shown in FIG. 3A and FIG. 3B, bushing 3300 may have a substantially cylindrical structure. The bushing 3300 may comprise a primary section 3306 and an annular lip 3302. The annular lip 3302 may be disposed at a first end 3304 of the bushing 3300. The annular lip 3302 may provide for an expanded region to allow for greater ease of manipulation and handling of the annular lip 3302.

The primary section 3306 may comprise a diameter of about 12.7 mm to about 14.3 mm, and a length of about 7 mm to about 10 mm. In some embodiments, the primary section 3306 may have a length of about 8.5 mm. The annular lip 3302 may comprise a diameter of about 19 mm to about 25 mm, and a length or thickness of about 2 mm to about 5 mm. In some embodiments, the annular lip 3302 may have a length of about 4 mm. The annular lip 3302 may comprise a diameter at least as large as, or larger than the diameter of the first section 1104 of the inner recess 1102 of the sleeve 1100. In this manner, the annular lip 3302 may not be able to enter or otherwise fit into the inner recess 1102. In contrast, the primary section 3306 may be sized and/or configured to be received into the first section 1104 of the inner recess 1102 of the sleeve 1100.

Bushing 3300 may further comprise a passageway 3312 extending through a length of the bushing 3300. A plurality of internal threads 3308 may be disposed within the passageway 3312 and may span a length of about 7 mm to about 10 mm. In some embodiments, the plurality of internal threads may span a length of about 7.5 mm. The plurality of internal threads 3308 may extend from the first end 3304 of the bushing 3300 towards a second end 3310 of the bushing 3300. The plurality of internal threads 3308 may not extend all the way to the second end 3310 of the bushing 3300. The plurality of internal threads 3308 may be configured to mate with the second external threads 2220 of the second threaded section 2206 of the shaft 2200. In operation, the bushing 3300 may be lowered or otherwise positioned through the first end 2208 of the shaft 2200. A diameter of the passageway 3312 may be greater than a diameter of the first threaded section 2204 of the shaft 2200. Thus, the bushing 3300 may directly slide past the first threaded section 2204. The second threaded section 2206 and the passageway 3312 may be sized so that the internal threads 3308 of the bushing 3300 can be secured or fastened against the second external threads 2220 of the shaft 2200.

Bushing 3300 may further comprise an unthreaded region 3314, which may be part of the passageway 3312. The unthreaded region 3314 may be disposed a second end 3316 of the bushing 3300. The unthreaded region 3314 may be sized and/or configured to receive at least a portion of the interior section 2202 therein. The unthreaded region 3314 may have a depth of about 3 mm to about 9 mm. In some embodiments, the unthreaded region 3314 may have a depth of about 5 mm.

Bushing 3300 may further comprise at least one notch 3318 at the second end 3316. Notch 3318 may comprise a small indentation of a particular geometry. For example, in some embodiments, notch 3318 may have a triangular geometry. Notch 3318 may provide a mechanical or sensory feedback as bushing 3300 is rotated. A user may sense a "click" or other sensory feedback when notch 3318 contacts another component of the external fixation strut. For example, the presence of one notch 3318 at the second end 3316 may indicate that one full turn has been made to the bushing 3300 when the sensory feedback is received. In some embodiments, notch 3318 may be a V-shaped or a C-shaped notch. A V-shaped notch may advantageously provide the necessary amount of sensory feedback without impeding or creating difficulties with the rotation of bushing 3300. Notch 3318 may not extend all the way across the material. In some embodiments, there may be additional notches. Depending on the position and number of notches 3318 disposed at second end 3316, sensory feedback may provide a user with additional information. For example, one notch may indicate that bushing 3300 has been rotated by 360 degrees, and will detent and "click" once each full revolution is effected. As another example, two equally-spaced notches may indicate that bushing 3300 has been rotated half a turn or 180 degrees, each time a sensory feedback or "click" is experienced. As another example, four equally-spaced notches may indicate that bushing 3300 has been rotated a quarter of a turn or 90 degrees, each time a sensory feedback or "click" is experienced. The notch 3318 may also advantageously set the bushing 3300 in a particular position and prevent undesired or accidental turning of bushing 3300.

In some embodiments, bushing 3300 may comprise low-friction materials. For example, bushing 3300 may comprise PEEK plastic. Bushing 3300 comprising low-friction materials may advantageously provide for smoother rotation against metallic components of the external fixation strut.

Figure 4:
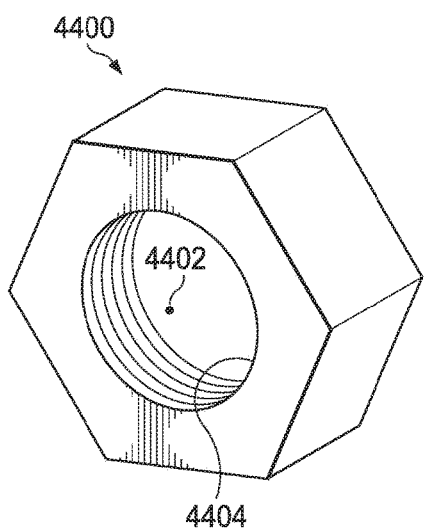
FIG. 4 illustrates a nut according to a specific example embodiment of the disclosure.

An external fixation strut according to embodiments of the present disclosure may further comprise a nut. FIG. 4 depicts a nut 4400 of an external fixation strut according to an embodiment of the present disclosure. The nut 4400 may have a length of about 3 mm to about 7 mm. In some embodiments, the nut 4400 may have a length of about 5 mm. A center recess 4402 of the nut 4400 may have a diameter of about 5 mm to about 10 mm. In some embodiments, the center recess 4402 may have a diameter of about 6 mm. Internal threads 4404 may be disposed within the center recess 4402. The internal threads 4404 may be sized and/or configured so as to mate with the first external threads 2218 of the first threaded section 2204. In this manner, the internal threads 4404 of the nut 4400 may be secured and/or fastened against the first external threads 2218 of the shaft 2200.

A nut 4400 of the present disclosure may be of any number of particular geometries. In some embodiments, as depicted in FIG. 4, nut 4400 may have a hexagonal geometry. However, other geometries such as a pentagonal or rectangular geometry may also be appropriate. Geometries of nut 4400 may also advantageously provide for flat surfaces to interact with a manipulation device, such as a wrench. For example, a wrench may contact the flat surfaces of a hexagonal nut 4400 to facilitate rotation or manipulation of nut 4400.

As described above, in some embodiments, the first threaded section 2204 and the second threaded section 2206 may have the same diameters and the same threading dimensions. Such embodiments may advantageously provide for greater ease of manufacturing the components of an external fixation strut. However, such embodiments may require that certain features, such as nut 4400 be secured into a particular position along the first threaded section 2204 in order to prevent nut 4400 from advancing into the second threaded section 2206. Securing nut 4400 may be accomplished by welding, pinning, or chemical retaining agent (e.g. Locktight™).

Figure 5A:
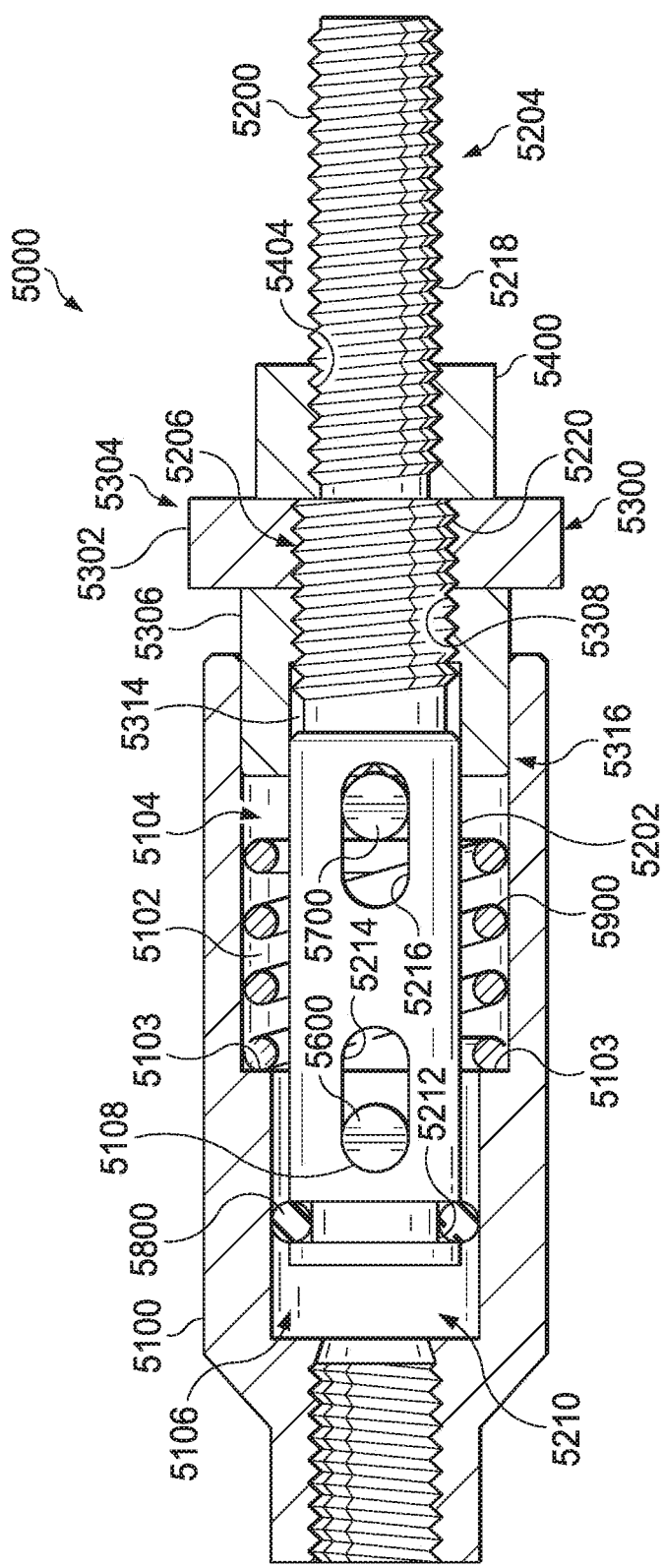
FIG. 5A illustrates an external fixation strut according to a specific example embodiment of the disclosure.

FIG. 5A depicts a partially assembled external fixation strut 5000 of the present disclosure. As depicted in FIG. 5A, a ring 5800, such as a Teflon™-O ring 5800, may be disposed within the annular indentation 5212 of the shaft 5200. Ring 5800 may be inserted and/or disposed within the annular indentation 5212 such that, upon assembly, ring 5800 is secured within the external fixation strut 5000 and cannot be readily removed from the apparatus. In some embodiments, ring 5800 may be a C-ring. In some embodiments, ring 5800 may comprise or may be produced from low friction materials. For example, ring 5800 may be composed of plastic (e.g. PEEK) that may provide for low friction interaction against surrounding components, and may advantageously provide for smoother dynamization as shaft 5200 moves relative to sleeve 5100 when an external force is exerted thereupon.

A biasing pin 5700 may be inserted into biasing pin longitudinal slot 5216 of the shaft 5200.

The shaft 5200 may be inserted into the sleeve 5100 so that at least a portion of the interior section 5202 is received into the second section 5106 of the inner recess 5102 of the sleeve 5100. The sleeve 5100 may also comprise first section 5104. Embodiments of the present disclosure advantageously provide for a holding pin hole 5108 and a holding pin longitudinal slot 5214, wherein the holding pin hole 5108 may align with at least a portion of the holding pin longitudinal slot 5214. In this manner, a holding pin 5600 may be inserted through both the holding pin hole 5108 and the holding pin longitudinal slot 5214. The holding pin 5600 may have a diameter of about 3.2 mm and a length of about 15.8 mm. In some embodiments, the holding pin 5600 may have the same diameter as the holding pin hole 5108 of the sleeve 5100.

In some embodiments, the inserted holding pin 5600 may extend through both sides of the sleeve 5100, the second section 5106 of the inner recess 5102 of the sleeve 5100, and the holding pin longitudinal slot 5214 of the shaft 5200. In operation, a holding pin 5600 inserted in the above described manner may secure the shaft 5200 into the sleeve 5100 so that the shaft 5200 may only have translational freedom along a longitudinal axis of the external fixation strut. The translational freedom available to the shaft 5200 may be limited by the length of the holding pin longitudinal slot 5214. The translational freedom of the shaft 5200 may correspond to the degree or amount of dynamization available to the external fixation strut. Dynamization may be afforded based on the amount of compressive forces that are applied to the shaft 5200.

As depicted in FIG. 5A, an external fixation strut of the present disclosure may comprise bushing 5300. The bushing 5300 may be secured against the shaft 5200. For example, a plurality of internal threads 5308 may be secured against a second threaded section 5206 of the shaft 5200. A primary section 5306 of the bushing 5300 may be disposed within the first section 1104 of the inner recess 1102 of the sleeve 5100. In some embodiments, a first end 5304 of the bushing 5300 may be in contact with a nut 5400. In some embodiments, bushing 5300 may not contact nut 5400. A second end 5316 of the bushing 5300 may be in contact with the biasing pin 5700. A portion of the interior section 5202 and/or a portion of the second threaded section 5206 of the shaft 5200 may be disposed within an unthreaded region 5314 of the bushing 5300.

An annular lip 5302 of the bushing 5300 may allow for easier manipulation of the bushing 5300. For example, rotation of the annular lip 5302 may result in rotation of the bushing 5300 as a whole and may result in movement of the bushing 5300 along a length of the second threaded section 5206 of the shaft 5200. Depending on the position of the bushing 5300 relative to the second threaded section 5206, more or less of second external threads 5220 may be positioned within the unthreaded region 5314 of the bushing 5300. Further, depending on the position of the bushing 5300 relative to the second threaded section 5206, more or less dynamization may be afforded to the external fixation strut. When the bushing 5300 is fully fastened, the annular lip 5302 may be in contact with certain portions of the sleeve 5100. In a fully fastened state, the external fixation strut may have little to no dynamization available. In a fully fastened state, the shaft 5200 may have little to no movement or translational freedom relative to the sleeve 5100.

As depicted in FIG. 5A, an external fixation strut of the present disclosure may comprise nut 5400. Nut 5400 may be secured against first threaded section 5204 of the shaft 5200. Internal threads 5404 of the nut 5400 may be fastened against first external threads 5218 of the first threaded section 5204. A larger diameter of the second threaded section 5206 may prevent the nut 5400 from being further fastened along a length of the shaft 5200. When the nut 5400 is secured against a base of the first threaded section 5204, the nut 5400 may advantageously secure bushing 5300 in place against the second threaded section 5206. Nut 5400 may or may not be in contact with bushing 5300. In practice, the nut 5400 prevents bushing 5300 from being overly loosened or otherwise removed from the second threaded section 5206. In some embodiments, the position of nut 5400 along the first threaded section 5204 may be secured. Securing nut 5400 against the first threaded section 5204 may be accomplished by difference methods, including welding or using a securing pin.

External fixation strut of the present disclosure may further comprise a biasing member 5900. In some embodiments, the biasing member 5900 may be a spring (e.g. coil spring, wave spring, etc.). The spring used may have a particular spring constant. For example, in some embodiments, the spring used as a biasing member 5900 may have a spring constant of about 3.75 pounds/mm. In some embodiments, the spring used as a biasing member 5900 may have a spring constant of about 3.50 pounds/mm to about 4 pounds/mm. A spring is described herein by way of example. One of ordinary skill in the art having the benefit of the present disclosure would appreciate other components that may be used to achieve a biasing effect as described herein.

In some embodiments, the biasing member 5900, such as a spring, may be disposed around the interior section 5202 of the shaft 5200. For example, a spring may coil around the interior section 5202 of the shaft 5200. When the external fixation strut is assembled, the biasing member 5900 may thus be disposed around the interior section 5202 and within the inner recess 5102 of the sleeve 5100. Further, the biasing member 5900 may be positioned such that it is in contact with the biasing pin 5700 at one end, and may bias against a shoulder 5103 of the inner recess 5102 at an opposite end. The biasing member 5900 may exert an expansive force when compressed. Consequently, the biasing member 5900 may exert an expansive force against the biasing pin 5700 and the sleeve 5100.

In operation, bushing 5300 may be manipulated so that the plurality of internal threads 5308 of the bushing 5300 may be rotated against the second threaded section 5206 of the shaft 5200. If bushing 5300 is fastened downward towards the sleeve 5100, bushing 5300 may exert a compressive force or a pressure against biasing pin 5700, which may in turn exert a compressive force or a pressure against the biasing member 5900. Depending on the amount of compressive force present, biasing member 5900 may allow for a particular range of compression.

The arrangement of the holding pin 5600, holding pin hole 5108, and the holding pin longitudinal slot 5214 allows for translational movement of the sleeve 5100 relative to the shaft 5200. Thus, the amount of compressive force on the biasing member 5900 may correspond to the amount of expansion available to the biasing member 5900, which may in turn correspond to the amount of translational movement of the sleeve 5100 relative to the shaft 5200.

In operation, rotation of bushing 5300 may adjust the degree of amount of dynamization available to the external fixation strut. In some embodiments, the amount of dynamization available may range from 0 mm to 3 mm. Further, each full turn of the bushing 5300 may correspond to 1 mm of dynamization for the external fixation strut. Each full turn of the bushing 5300 may allow for 1 mm of relative translational movement between the sleeve 5100 and the shaft 5200.

When the bushing 5300 is fully fastened, the annular lip 5302 may be in contact with certain portions of the sleeve 5100. In a fully fastened state, biasing member 5900 may be fully compressed within the inner recess 5102 of the sleeve 5100. Shaft 5200 may be disposed in a manner such that second end 5210 of the shaft 5200 may contact a surface of the inner recess 5102 of the sleeve 5100. In this state, little to no dynamization may be available to the external fixation strut. There may be little to no translation movement available to the sleeve 5100 relative to the shaft 5200.

When the bushing 5300 is fully loosened, the annular lip 5302 may be in contact with the nut 5400. In a fully loosened state, biasing member 5900 may be fully expanded within the inner recess 5102 of the sleeve 5100, or may be as expanded as allowable within the inner recess 5102 of the sleeve 5100. In this state, a compressive force along a longitudinal direction of the external fixation strut may lead to movement of the sleeve 5100 relative to the shaft 5200. In some embodiments, the amount of movement available may correspond to the length of holding pin longitudinal slot 5214, or the longitudinal movement available to holding pin 5600 within holding pin longitudinal slot 5214.

Embodiments of the present disclosure may advantageously provide for an external fixation strut wherein the length of external fixation strut does not vary depending on whether bushing 5300 is fastened or loosened, or how far along the second threaded section 5206 the bushing 5300 is fastened or loosened. Depending on how far along the second threaded section 5206 the bushing 5300 is fastened or loosened, the external fixation strut may provide for more dynamization or may allow for compression the sleeve 5100 relative to the shaft 5200. However, the length of the external fixation strut in an uncompressed state may be independent of whether the bushing 5300 is fastened or loosened. Rather, any change in the length of the strut may occur as a result of external compressive forces acting upon it. In some embodiments, a length of an external fixation strut in an uncompressed state may be about 50 mm. The range of dynamization allowed may be about 0 mm to about 3 mm. The range of dynamization afforded to the external fixation strut may be limited by the distance between a face/end of bushing 5300 and the end of sleeve 5100.

Figure 5B:
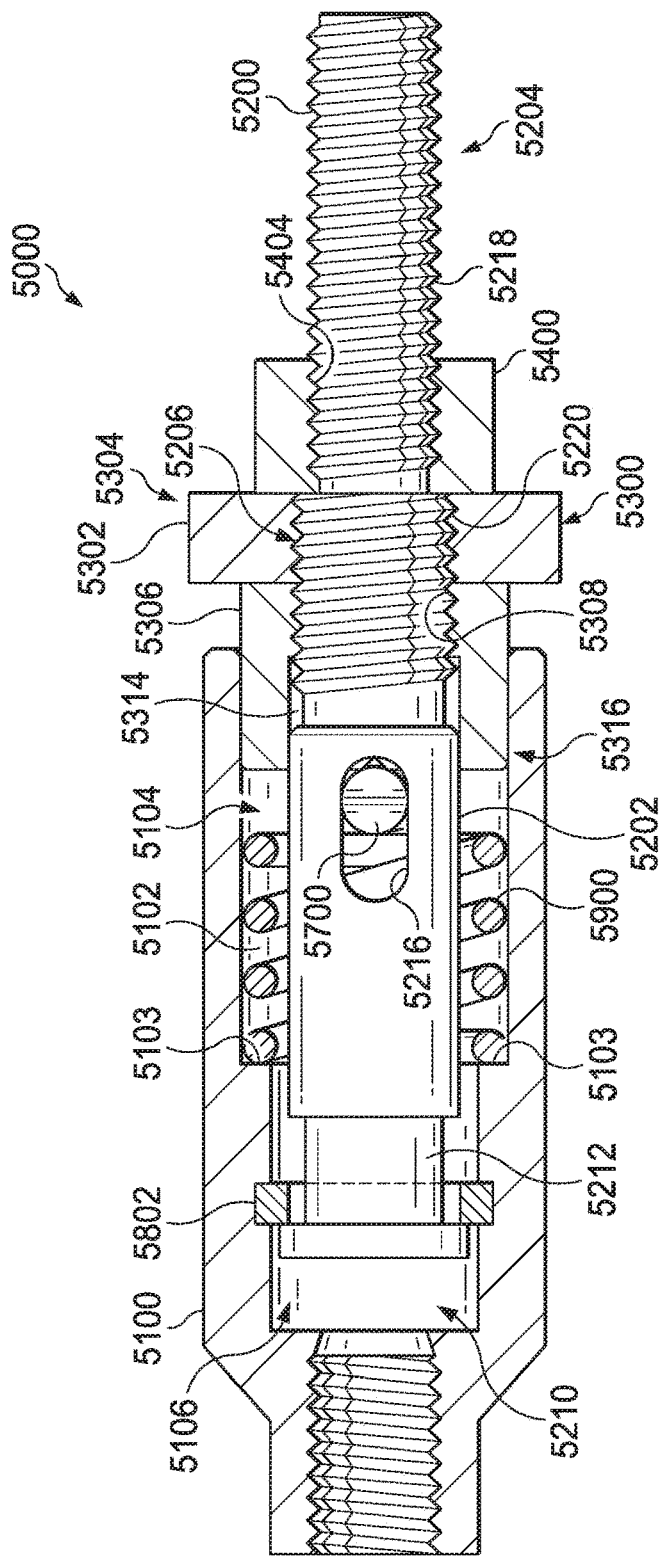
FIG. 5B illustrates an external fixation strut according to a specific example embodiment of the disclosure.

The present disclosure provides for various embodiments of external fixation struts. FIG. 5B depicts an alternative embodiment of the present disclosure. The external fixation strut 5000 in FIG. 5B may provide for many of the features described above and depicted in FIG. 5A. However, the example embodiment of FIG. 5B may not comprise the holding pin 5600, holding pin hole 5108, and the holding pin longitudinal slot 5214 of the embodiment of FIG. 5A. The absence of said features may advantageously prevent or reduce torsional stress or torsional binding of the shaft 5200 relative to the sleeve 5100. The embodiment of FIG. 5B advantageously allows for axial rotation of the shaft 5200 relative to the sleeve 5100.

As depicted in FIG. 5B, embodiments may provide for a longer annular indentation 5212 of shaft 5200. Annular indentation 5212 may have a length of about 5 mm. Retaining ring 5802 may be a component such as a ID/OD lock retaining ring. A length of annular indentation 5212 may be greater than a width of thickness of the retaining ring 5802 disposed against it. In this manner, shaft 5200 may be allowed to translate along the longitudinal direction of the sleeve 5100 while the retaining ring 5802, secured against the annular indentation 5212, prevents the shaft 5200 from being completely withdrawn or disassembled from the sleeve 5100. The retaining ring 5802 may also be completely or partially secured and/or disposed within an indentation along the inner wall of the sleeve 5100. In some embodiments, the amount of movement along the longitudinal direction of the shaft 5200 within the sleeve 5100 may be limited, at least in part, by a length of the annular indentation 5212. Retaining ring 5802 may comprise low frictional material, such as PEEK plastic, to provide for smooth translation of shaft 5200 within sleeve 5100.

Figure 5C:
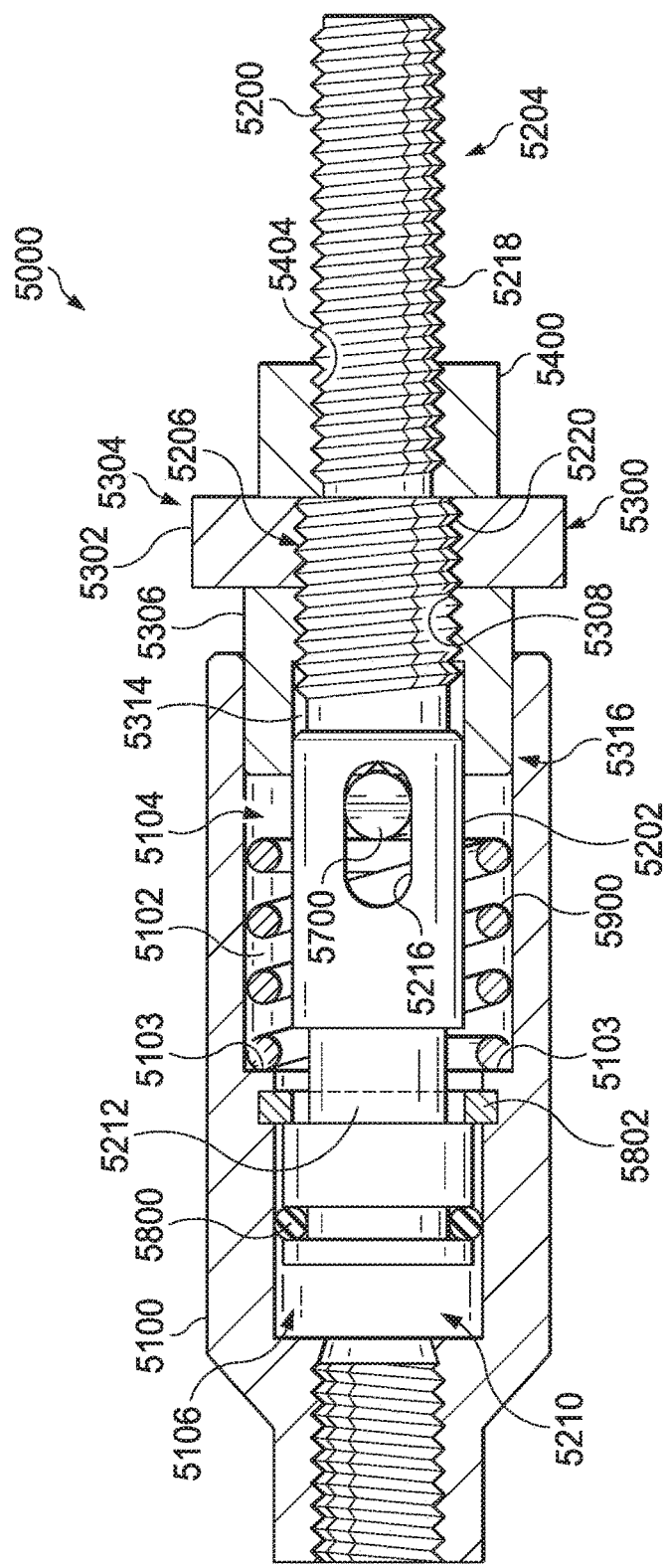
FIG. 5C illustrates an external fixation strut according to a specific example embodiment of the disclosure.

FIG. 5C depicts an alternative embodiment of the present disclosure. The external fixation strut 5000 in FIG. 5C may provide for many of the features described above and depicted in FIG. 5A and FIG. 5C. However, the example embodiment of FIG. 5C may not comprise the holding pin 5600, holding pin hole 5108, and the holding pin longitudinal slot 5214 of the embodiment of FIG. 5A. The absence of said features may advantageously prevent or reduce torsional stress or torsional binding of the shaft 5200 relative to the sleeve 5100. The embodiment of FIG. 5C advantageously allows for axial rotation of the shaft 5200 relative to the sleeve 5100.

As shown, embodiments may advantageously comprise both ring 5800 and retaining ring 5802. As described above, ring 5800 may be a Teflon™-O ring. Ring 5800 may serve as a guide bushing. In some embodiments, ring 5800 may comprise low frictional material, such as PEEK plastic, to provide for smooth translation of shaft 5200 within sleeve 5100. The embodiment of FIG. 5C may also comprise retaining ring 5802. Retaining ring 5802 may be disposed in the elongated annular indentation 5212 of shaft 5200. Annular indentation 5212 may have a length of about 3 mm to about 5 mm. As described above, retaining ring 5802 may be a component such as a ID/OD lock retaining ring. Shaft 5200 may be allowed to translate along the longitudinal direction of the sleeve 5100 while the retaining ring 5802, secured against the annular indentation 5212, prevents the shaft 5200 from being completely withdrawn or disassembled from the sleeve 5100. The retaining ring 5802 may also be completely or partially secured and/or disposed within an indentation along the inner wall of the sleeve 5100. In some embodiments, the amount of movement along the longitudinal direction of the shaft 5200 within the sleeve 5100 may be limited, at least in part, by a length of the annular indentation 5212. Retaining ring 5802 may comprise low frictional material, such as PEEK plastic, to provide for smooth translation of shaft 5200 within sleeve 5100.

As seen from FIG. 5A, FIG. 5B, and FIG. 5C, embodiments of the present disclosure may provide for compression of a biasing member 5900 of an external fixation strut 5000. Compression of a biasing member 5900 may occur without a corresponding change in the position or movement of the shaft 5200 and sleeve 5100 with respect to one another. As a result, in an uncompressed state or a state without an external force exerted thereupon, a total length of the external fixation strut 5000 may remain constant as the biasing member 5900 is compressed or expanded. Any change in the length of the external fixation strut 5000 may occur as a result of external compressive forces acting upon it.

The present disclosure also provides for embodiments of external fixation struts as depicted in FIG. 6A and FIG. 6B. Embodiments of external fixation struts as depicted in FIG. 6A and FIG. 6B may comprise various components.

In some embodiments, an external fixation strut may comprise a sleeve 6100 as depicted in FIG. 6A and FIG. 6B. The sleeve 6100 may be substantially cylindrical in shape. The sleeve 6100 comprise an inner recess 6102, which may include a first section 6104 and a second section 6106. The first section 6104 and the second section 6106 may differ in size. In some embodiments, the first section 6104 may have a diameter that is larger than the diameter of the second section 6106. In this manner, components that may be secured in the first section 6104 may not fit or otherwise be received into the second section 6106. The first section 6104 may have a diameter of about 14 mm and a length of about 11.8 mm. The second section 6106 may have a diameter of about 12.7 mm and a length of about 25 mm. In some embodiments, the length of the inner recess 6102 may be about 25.2 mm and the length of the sleeve 6100 may be about 51 mm.

Sleeve 6100 may further comprise a narrowed section 6120 at a first end 6112. The first end 6112 may also comprise an opening 6110. The opening 6110 may allow various components of the external fixation strut to be received therein. Sleeve 6100 may also comprise a plurality of internal threads 6118 disposed at a second end 6116 of the sleeve 6100. The second end 6116 may be opposite to the previously discussed first end 6112 where the opening 6110 to the inner recess 6102 is disposed. A plurality of internal threads 6118 may be disposed at the second end 6116 of the sleeve 6100. The plurality of internal threads 6118 may allow an external fixation strut to be secured to an external fixation device. The plurality of internal threads 6118 may span a length of about 14 mm.

Sleeve 6100 may further comprise a narrowed section 6114 at a second end 6116 of the sleeve 6100. The narrowed section 6114 of the sleeve 6100 may have a width of about 10 mm to about 13 mm, and a length of about 8 mm to about 12 mm. The narrowed section 6114 may have a length of about 9.5 mm. In some embodiments, sleeve 6100 may further comprise indented surfaces 6115 at the narrowed section 6114. The indented surfaces 6115 may provide contact points for a wrench to be secured against the sleeve 6100 so rotation or other manipulation may be facilitated. Narrowed section 6114 may comprise, for example, two to six indented surfaces 6115. Indented surfaces 6115 may comprise a length of about 6 mm.

As depicted in FIG. 6A and FIG. 6B, some embodiments of the present disclosure may also comprise shaft 6200. The shaft 6200 may have a length of about 46 mm. Shaft 6200 may comprise a threaded section 6222 and an interior section 6226.

The threaded section 6222 may comprise a plurality of external threads 6224. The plurality of external threads 6224 may allow an external fixation strut to be secured to an external fixation device. The threaded section 6222 may have a diameter of about 6 mm and a length of about 22 mm.

The interior section 6226 may be a substantially cylindrical section that may be configured to be disposed at least partially within the inner recess 6102 of the sleeve 6100. The interior section 6226 may have a length of about 13.8 mm. In some embodiments, a portion of the interior section 6226 may be disposed within the inner recess 6102 and a portion of the interior section 6226 may be disposed outside of the inner recess 6102. In some embodiments, the interior section 6226 may comprise an annular protrusion 6228. The annular protrusion 6228 may provide for an expanded region that may be secured within the inner recess 6102 of the sleeve 6100. The annular protrusion 6228 may have a diameter of about 12.7 mm. In some embodiments, the annular protrusion 6228 may have the same diameter as the second section 6106 of the inner recess 6102. The annular protrusion 6228 may be disposed along the interior section 6226 of the shaft 6200 in such a manner so as to separate or define two segments of the interior section 6226. One side of the annular protrusion 6228 may comprise an end segment 6230, and an opposing side of the annular protrusion 6228 may comprise a primary segment 6232. The primary segment 6232 may be connected to the threaded section 6222. The end segment 6230 may be disposed within the inner recess 6102. In some embodiments, the primary segment 6232 and the end segment 6230 may have different diameters and lengths. The primary segment 6232 may have a diameter of about 6 mm and a length of about 35.8 mm. The end segment 6230 may have a diameter of about 4.7 mm and a length of about 7.7 mm.

In operation, the shaft 6200 may have a translational movement relative to the sleeve 6100. For example, if a compressive force is applied longitudinally to the shaft 6200, the shaft 6200 may move into or move further into inner recess 6102 of the sleeve 6100. Consistently, if a compressive force on the shaft 6200 is reduced, the shaft 6200 may return to a default position.

In some embodiments, the present disclosure may advantageously provide external fixation struts wherein the shaft 6200 may be free to rotate about a center axis of the sleeve 6100. The freedom of shaft 6200 to rotate may advantageously reduce or prevent torsional binding, which may adversely affect the ability of the shaft 6200 to translate within the sleeve 6100.

Some embodiments of the present disclosure may also comprise biasing member 6900. In some embodiments, the biasing member 6900 may be a spring. The spring used may have a particular spring constant. For example, in some embodiments, the spring used as a biasing member 6900 may have a spring constant of about 3.76 pounds/mm. In some embodiments, the spring used as a biasing member 6900 may have a spring constant of about 3.50 pounds/mm to about 4 pounds/mm. A spring is described herein by way of example. One of ordinary skill in the art having the benefit of the present disclosure would appreciate other components that may be used to achieve a biasing effect as described herein.

In some embodiments, the biasing member 6900, such as a spring, may be disposed around in the inner recess 6102 of the sleeve 6100. More specifically, biasing member 6900 may be disposed within the second section 6106 of the inner recess 6102 of the sleeve 6100. The biasing member 6900 may be positioned such that it is in contact with the annular protrusion 6228 at one end, and in contact with a contact feature 6920 at an opposite end. Further, the biasing member 6900 may be positioned such that the end segment 6230 of the shaft 6200 extends through an inner portion of the biasing member 6900. For example, end segment 6230 may extend through the hollow interior of a spring that is serving as a biasing member 6900.

The biasing member 6900 may exert an expansive force when compressed. Consequently, the biasing member 6900 may exert an expansive force against the annular protrusion 6228 and the contact feature 6920.

As described above, some embodiments of the present disclosure may also comprise contact feature 6920. Contact feature 6920 may be a mechanical component comprising an annular protrusion 6922 and a longitudinal segment 6924. The contact feature 6920 may be sized to fit within or be disposed within the inner recess 6102 of the sleeve 6100.

The annular protrusion 6922 may have a substantially circular or disc-like geometry. The annular protrusion 6922 may have a diameter of about 12.7 mm. In some embodiments, the annular protrusion 6922 may have the same diameter as the second section 6106 of the inner recess 6102.

The longitudinal segment 6924 may extend from the annular protrusion 6922 in a longitudinal direction of the external fixation strut. In some embodiments, the longitudinal segment 6924 may comprise a cylindrical geometry with a spacing 6926 therein. For example, the longitudinal segment 6924 may be a cylinder with a recess or hollowed portion in the center of said cylinder. The spacing 6926 may advantageously allow for the end segment 6230 of the shaft 6200 to be received therein. The spacing 6926 may be sized and/or shaped to be complimentary to the end segment 6230 of the shaft 6200. Thus, when the end segment 6230 is fully disposed in the spacing 6926, a secure fit may be provided between the two components. In some embodiments, when the end segment 6230 is fully disposed in the spacing 6926, the longitudinal segment 6924 may be in contact with the annular protrusion 6228 of the shaft 6200.

Some embodiments of the present disclosure may also comprise a rotatable feature 6940. The rotatable feature 6940 of the present disclosure may comprise a substantially spherical structure with specific sections removed along particular planes of the spherical structure. As a result, the rotatable feature 6940 may have a plurality of flat surfaces that have varying distances from a center 6944 of the rotatable feature 6940. Depending on which one of the plurality of flat surfaces is engaging or in contact with the contact feature 6920 within the inner recess 6102 of the sleeve 6100, a different amount of dynamization may be provided to the overall system.

More specifically, in some embodiments, the rotatable feature 6940 may comprise a plurality of surfaces 6942A, 6942B, and 6942C. As depicted in FIG. 6A and FIG. 6B, each of the plurality of surfaces 6942A, 6942B, and 6942C may have a different distance from the center 6944 of the rotatable feature 6940. For example, surface 6942A may be further from the center 6944 than either surface 6942B or 6942C. Thus, when rotatable feature 6940 is turned such that surface 6942A is in contact with contact feature 6920, a greater amount of compression may be provided to contact feature 6920 than when either surface 6942B or 6942C is in contact with contact feature 6920. As a result, biasing member 6900 may be relatively compressed, and little dynamization may be afforded to the system. In contrast, surface 6942C is closer to the center 6944 than either surface 6942A or 6942B. Thus, when rotatable feature 6940 is turned such that surface 6942C is in contact with contact feature 6920, relatively little compression may be provided to contact feature 6920 than when either surface 6942A or 6942B is in contact with contact feature 6920. As a result, biasing member 6900 may not be very compressed, and a considerable amount of dynamization may be afforded to the system.

As shown in FIG. 6A and FIG. 6B, an embodiment of the present disclosure may comprise the rotatable feature 6940 with three flat surfaces 6942A, 6942B, and 6942C, and wherein the fourth "side" of the feature 6940 is a curved surface or a spherical surface. However, FIG. 6A and FIG. 6B are provided by way of example only. In some embodiments, the rotatable feature 6940 may comprise two flat surfaces, four flat surfaces or five flat surfaces, each of which may be operable to engage or come into contact with contact feature 6920. In some embodiments, the rotatable feature 6940 may or may not have the curved surface or the spherical surface as depicted in FIG. 6A and FIG. 6B. Providing for various surfaces on the rotatable feature 6940 may advantageously allow for different surfaces with different distances from the center 6944 to be in contact with the contact feature 6920, thereby allowing different amounts of available dynamization or different amounts of compression of a shaft 6200 relative to a sleeve 6100. The amount of available dynamization or compression may result from compression or expansion of a biasing member 6900, such as a spring, within an inner recess 6102 of the sleeve 6100 and the length of space 6926. Further, rotation of the rotatable feature 6940 may result in movement of the contact feature 6920 within an inner recess 6102 of the sleeve 6100 and increase or decrease the length of space 6926. The contact feature 6920 may move longitudinally within an inner recess 6102 of the sleeve 6100 as rotatable feature 6940 is rotated to engage a particular surface with the contact feature 6920. In some embodiments, distances of the plurality of surfaces 6942A, 6942B, and 6942C from a center 6944 may include, for example, 3.35 mm, 4.35 mm, and 5.35 mm. While biasing member 6900 may exert a biasing force, the maximum longitudinal translation available for the shaft 6200 relative to the sleeve 6100 may be regulated and/or limited by the length of space 6926.

As shown in FIG. 6A and FIG. 6B, present embodiments may also comprise an interior component 6950. The interior component 6950 may be a monolithic component configured to be disposed within the first section 6104 of the inner recess 6102 of the sleeve 6100. The interior component 6950 may be in contact with the annular protrusion 6228 and the narrowed section 6120 at the first end 6112 of the sleeve 6100. The narrowed section 6120 may advantageously secure the interior component 6950 within the first section 6104 of the inner recess 6102 of the sleeve 6100. Further, interior component 6950 may also serve as a linear guide bushing. In some embodiments, interior component 6950 may comprise and/or be manufactured from low friction material such as PEEK plastic.

Figure 6C:
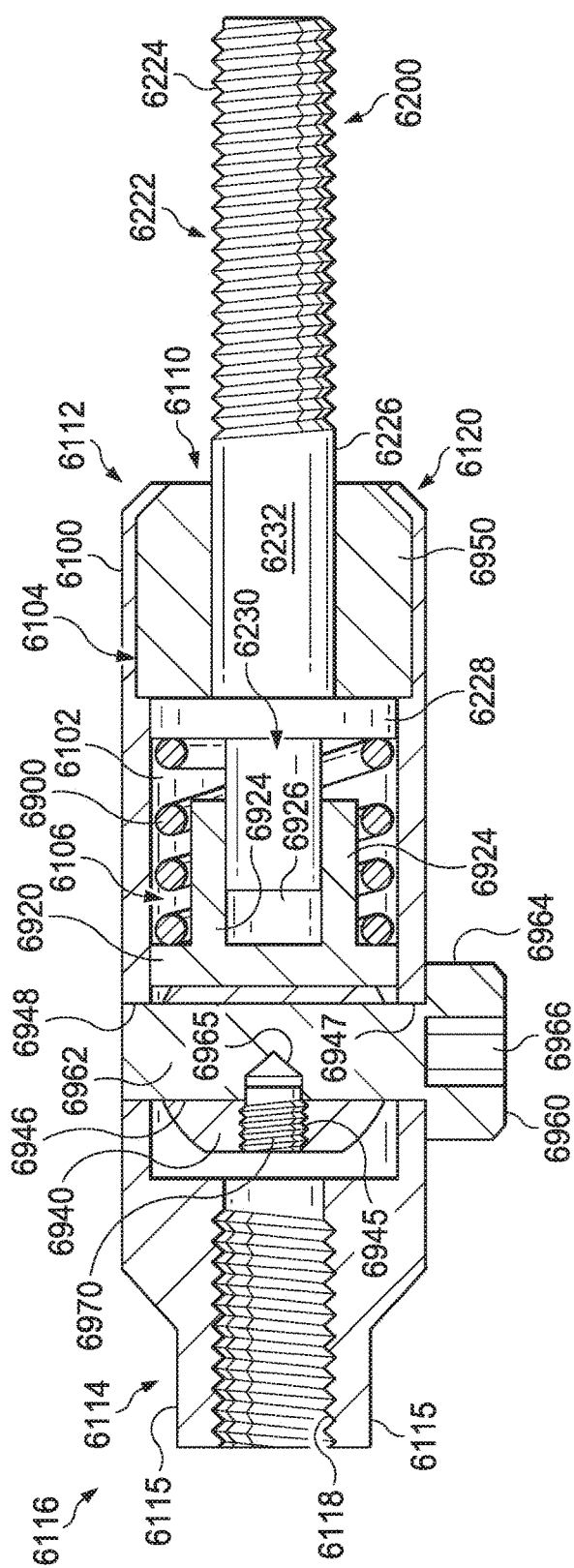
FIG. 6C illustrates an external fixation strut according to a specific example embodiment of the disclosure.

Additional features that may be used in the embodiments depicted in FIG. 6A and FIG. 6B are depicted in FIG. 6C. As shown in FIG. 6C, embodiments of the present disclosure may comprise a rotation mechanism 6960 and a set screw 6970. Further, the above-described rotatable feature 6940 may comprise a center channel 6948. The center channel 6946 may run along the rotatable feature 6940 to provide for a first opening 6947 and a second opening 6948. The center channel 6946 may pass through the center 6944 of the rotatable feature 6940. The rotatable feature 6940 may further comprise a set screw receiving recess 6945. The center channel 6946 and the set screw receiving recess 6945 may provide a mechanism to secure and turn the rotatable feature 6940 within the second section 6106 of the inner recess 6102.

Rotation mechanism 6960 may be inserted into the center channel 6946 of the rotation feature 6940. Rotation mechanism 6960 may then facilitate turning of the rotatable feature 6940. For example, rotation mechanism 6960 may comprise a body 6962, which may be disposed within the center channel 6946, and a head 6964, which may be disposed on the exterior of an external fixation strut. The head 6964 may comprise a geometry that may facilitate rotation of the rotation mechanism 6960. For example, the head 6964 may have a hexagonal or pentagonal geometry whereby the flat surfaces provided by way of the geometry can mate or interface with a wrench or other instrument. The wrench or other instrument can then manipulate the orientation of the head 6964, which in turn rotates the rotation mechanism 6960, which in turn rotates the rotatable feature 6940. Rotation of the rotation mechanism 6960 can be accomplished by other means. For example, the head 6964 may comprise an indent 6966, which may have a particular geometry to mate with an instrument. Rotation of said instrument can then facilitate rotation of the rotation mechanism 6960.

The position of the rotation mechanism 6960 within the center channel 6946 of the rotation feature 6940 can be secured using the set screw 6970. The set screw 6970 may be positioned into the interior of sleeve 6100 through the opening provided by the plurality of internal threads 6118 at the second end 6116. The set screw receiving recess 6945 of the rotatable feature 6940 can be aligned with a set screw receiving recess 6965 of the rotation mechanism 6960. Then, the set screw 6970 can be fastened or secured within the aligned set screw receiving recesses 6945, 6965.

The embodiments of FIG. 6A, FIG. 6B, and FIG. 6C advantageously provides for an external fixation strut with no pins or slots. Thus, dynamization may be provided without the need for alignment, replacement, or otherwise manipulation of small pins or slots. In operation, a practitioner may adjust the amount of dynamization of an external fixation strut by rotating or otherwise manipulating the rotatable feature 6940. For example, a practitioner may rotate the rotation mechanism 6960 to rotate or otherwise adjust the orientation of the rotatable feature 6940. Depending on which surface (e.g. the plurality of surfaces 6942A, 6942B, and 6942C) is in contact with contact feature 6920, the contact feature 6920 may have a different position within the second section 6106 of the inner recess 6102 of the sleeve 6100. Consequently, depending on the position of the contact feature 6920 within the second section 6106, a different amount of compression may be exerted on biasing member 6900.

When a great amount of compression is exerted on biasing member 6900, biasing member 6900 may be fully compressed between the annular protrusion 6228 and the contact feature 6920. In this situation, little to no dynamization may be provided to or available to the external fixation strut.

When the amount of compression exerted on biasing member 6900 is little or none, biasing member 6900 may be fully expanded between the annular protrusion 6228 and the contact feature 6920. In this situation, a great amount of dynamization may be provided to or available to the external fixation strut.

Figure 7A:
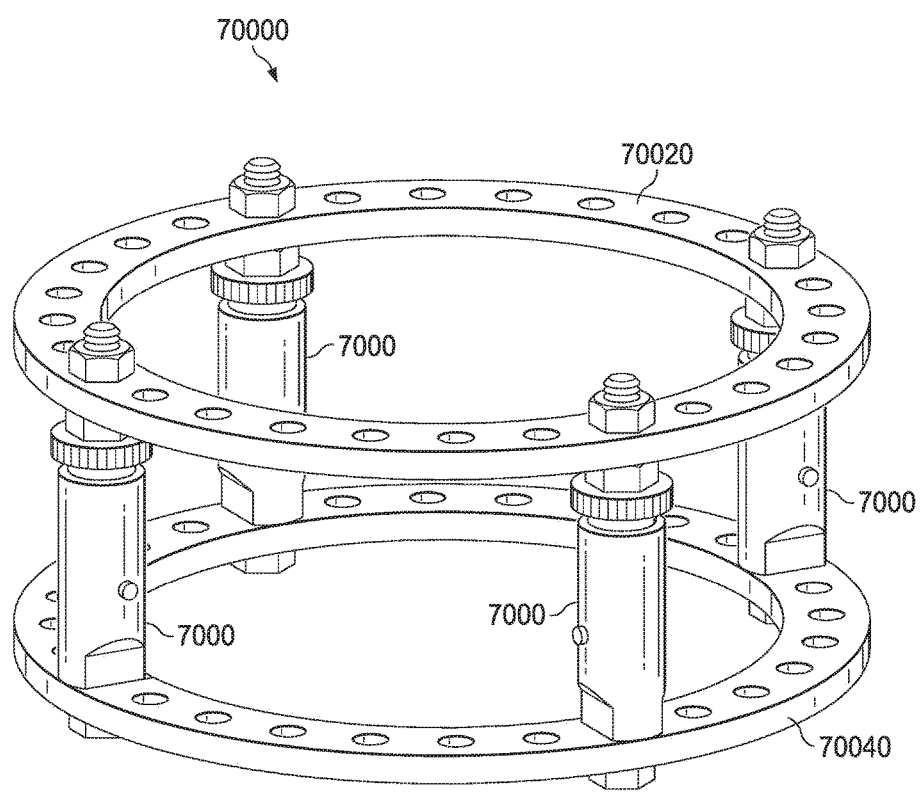
FIG. 7A illustrates a perspective view of an example external fixation device comprising external fixation struts according to a specific example embodiment of the disclosure.

Embodiments of the present disclosure provide for external fixation struts 7000 that may be used as part of an external fixation device 70000. FIG. 7A illustrates a perspective view of an example external fixation device comprising external fixation struts according to a specific example embodiment of the disclosure. As depicted, the external fixation device 70000 may comprise four external fixation struts 7000. However, fewer or more external fixation struts 7000 may be utilized (e.g. two, three, five, six).

The external fixation device 70000 may comprise a first external fixation ring 70020 and a second external fixation ring 70040 that surround a bone (not shown). The first external fixation ring 70020 and the second external fixation ring 70040 are connected by the external fixation struts 7000. The external fixation struts 7000 may be connected to the external fixation rings 70020, 70040 by various methods. In some embodiments, each of the external fixation struts 7000 may comprise a first articulatable ball joint (not shown) attached at each end of the external fixation struts 7000. In some embodiments, the first articulatable ball joint houses a first ball (not shown). The first ball (not shown) includes a first ball stud (not shown) that passes through a slot (not shown) into a threaded aperture in each of the external fixation rings 70020, 70040.

Figure 7B:
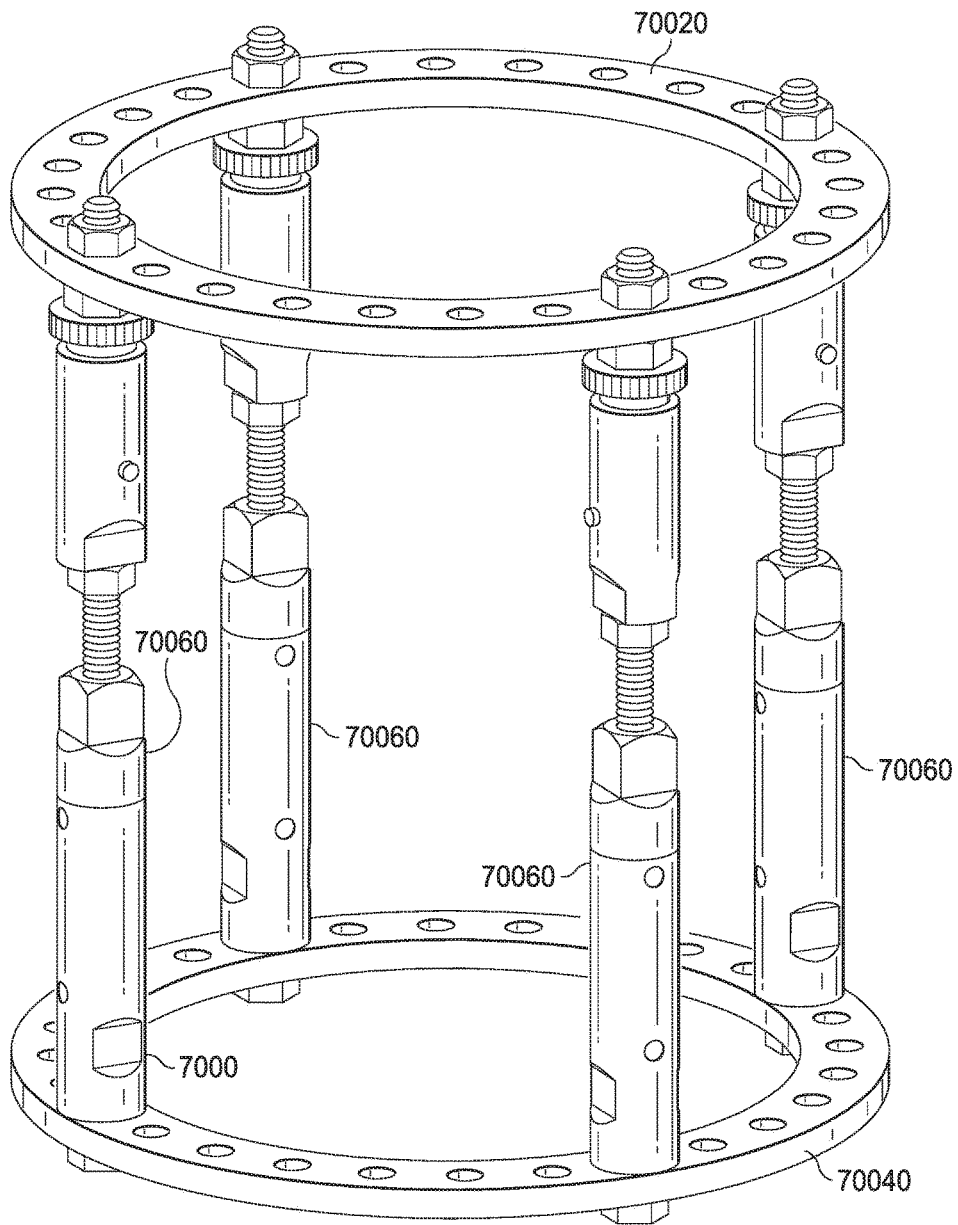
FIG. 7B illustrates a perspective view of an example external fixation device comprising external fixation struts according to a specific example embodiment of the disclosure.

FIG. 7B illustrates a perspective view of another example external fixation device 70000 comprising external fixation struts 7000 according to a specific example embodiment of the disclosure. In addition to the components depicted in FIG. 7A, the example embodiment of FIG. 7B may further comprise a plurality of external fixation rods 70060. The use of an external fixation rod 70060 may provide several advantages such as the lengthening and adjustment of the distance between the first external fixation ring 70020 and the second external fixation ring 70040; the rapid or gradual length adjustment between the first external fixation ring 70020 and the second external fixation ring 70040; and other manipulation of the orientations of the first external fixation ring 70020, the second external fixation ring 70040, and the various external fixation devices 70000 secured thereon. External fixation rod 70060 may be secured at one end to one of the first external fixation ring 70020 or the second external fixation ring 70040, and at another end of one of the plurality of external fixation struts 7000. As depicted, four external fixation rods 70060 may be used, with one corresponding to each of the four utilized external fixation struts 7000. However, the number of external fixation rods 70060 may vary. For example, in some embodiments, an external fixation device 70000 may comprise eight external fixation rods 70060, with one secured to each end of an external fixation strut 7000.

In some embodiments, an external fixation rod 70060 may be that of the external fixation connection rod described in U.S. Pat. No. 8,574,232, entitled External Fixation Connection Rod for Rapid and Gradual Adjustment, the disclosure of which is incorporated by reference in its entirety. Use of the external fixation connection rod described therein as external fixation rod 70060 may advantageously provide for a greater length between the first external fixation ring 70020 and the second external fixation ring 70040. Further, use of the external fixation connection rod described therein as external fixation rod 70060 may provide for greater ease in assembling the external fixation device on a patient, or adjusting the external fixation device once secured on a patient.

The use of the disclosure in U.S. Pat. No. 8,574,232 as the external fixation rod 70060 is provided by way of example only. One of ordinary skill in the art having the benefit of the present disclosure would appreciate that an external fixation rod 70060 may comprise more or less features than that disclosed in U.S. Pat. No. 8,574,232. For example, in some embodiments, providing for various rotating members or articulatable joints in an external fixation rod 70060 may advantageously allow for greater manipulation and/or adjustment of the external fixation device 70000 and the components therein. In other embodiments, utilizing an external fixation rod 70060 with fewer articulatable joints or rotating members may advantageously maintain parallel orientation of the first external fixation ring 70020 and the second external fixation ring 70040. Further, utilizing an external fixation rod 70060 with fewer articulatable joints or rotating members may advantageously stabilize or maintain the direction or axis of dynamization provided by the external fixation struts 7000.

Figure 8A:
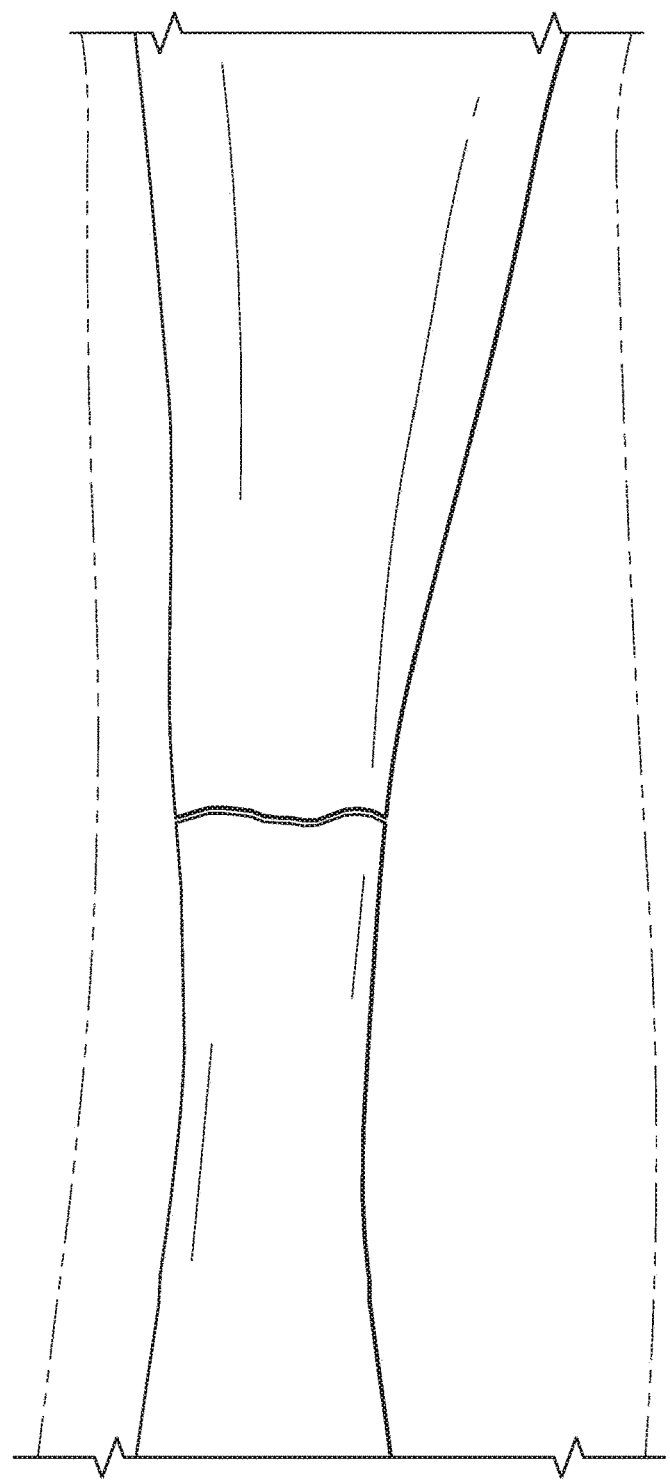
FIG. 8A illustrates a section of a person's bone with a fracture.

FIG. 8A illustrates a section of a person's bone with a fracture. The bone may be a femur, tibia, or fibula. As depicted in FIG. 8A, the bone may have one or more fractures. In an example embodiment, the fracture may be a midshaft tibial fracture that requires treatment and healing. In other embodiments, the bone may belong to other parts of the person's body.

Figure 8B:
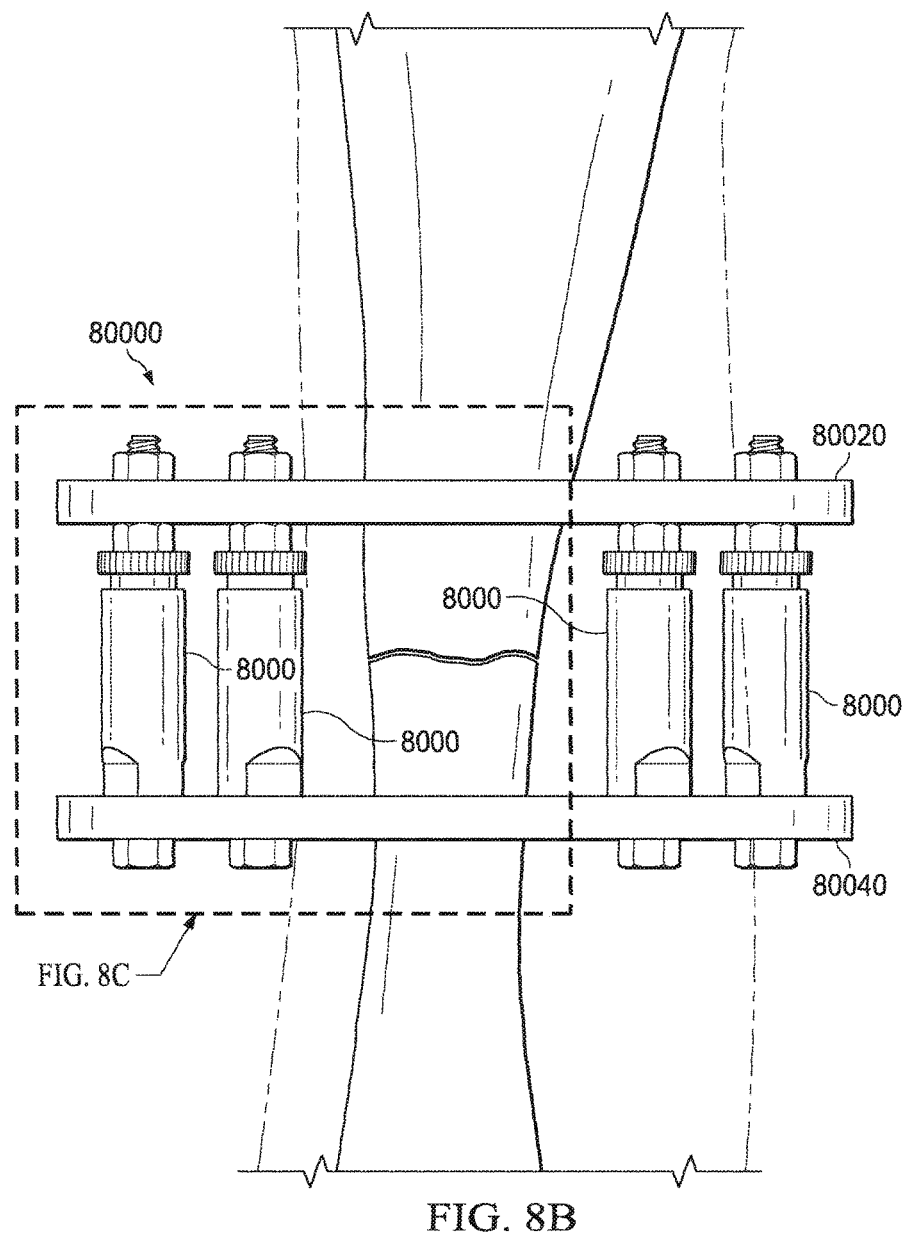
FIG. 8B illustrates an example embodiment of an external fixation device surrounding a person's bone with a fracture.
Figure 8C:
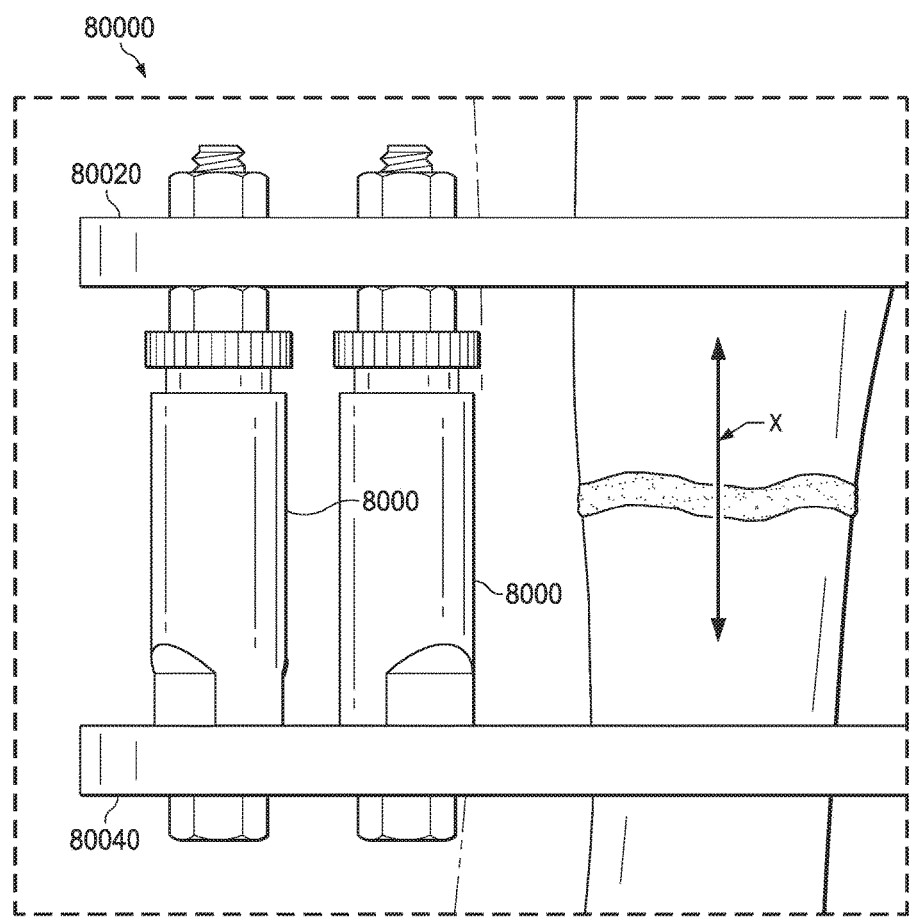
FIG. 8C illustrates a close up view of an example embodiment of an external fixation device surrounding a person's bone with a fracture.

FIG. 8B illustrates an external fixation device 80000 surrounding a person's bone with a fracture. FIG. 8C illustrates a close up view of an external fixation device 80000 surrounding a person's bone with a fracture. As depicted, a plurality of external fixation struts 8000 may be installed or secured to a first external fixation ring 80020 and a second external fixation ring 80040 that surround the bone. The external fixation struts 8000 shown in FIG. 8B and FIG. 8C may be the same as any one of the embodiments disclosed and described above, or any one of the embodiments depicted in FIG. 5A, FIG. 5B, FIG. 6A, FIG. 6B, and/or FIG. 6C. The bone shown may be a femur, tibia, or fibula. In other embodiments, the bone may belong to other parts of the person's body. Since the bone shown in FIG. 8B and FIG. 8C can represent various bones of a person's body, in certain embodiments, the dimensions of the bone may be slightly out of proportion. In an embodiment, pins (not shown) attached to the external fixation device 80000 are connected to the bones near a fracture that requires healing (e.g. person's tibia). The pins (not shown) may be drilled or pierced into the person's skin and bone for installation of the external fixation device 80000. Connection of the external fixation device 8000 to the bone(s) may include placing connectors, such as wires, pins, screws, and/or rods, among others through the skin and into, through, and/or around the selected bone(s).

In some embodiments, the external fixation struts 8000 may advantageously be positioned parallel to one another. In some embodiments, the first external fixation ring 80020 and the second external fixation ring 80040 may be positioned parallel to one another, and the external fixation struts 8000 may advantageously be positioned orthogonal to a plane of the first external fixation ring 80020 and the second external fixation ring 80040. Such arrangements may advantageously provide for controlled dynamization along a longitudinal axis of the direction of the external fixation struts 8000.

Figure 8E:
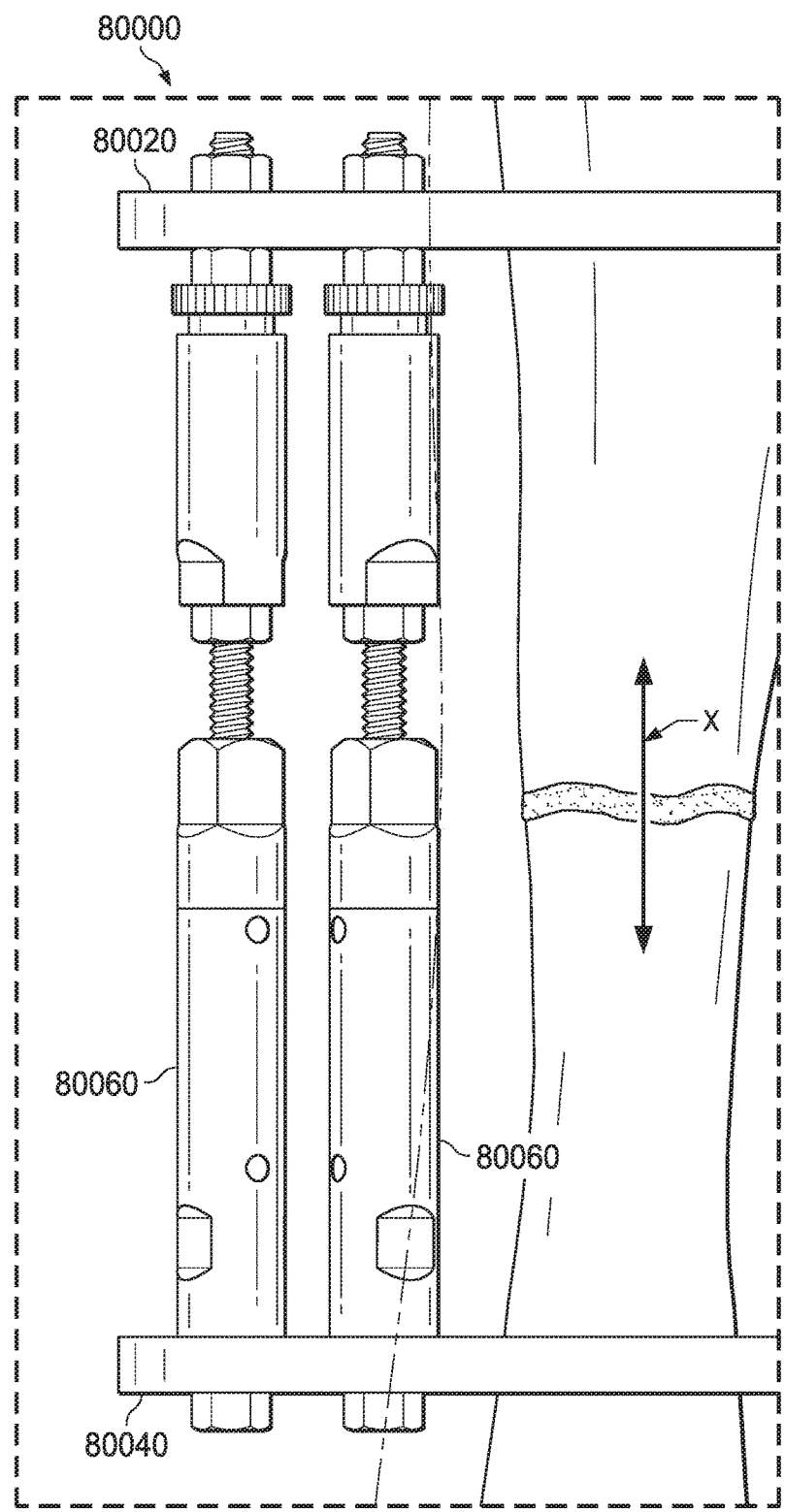
FIG. 8E illustrates a close up view of an example embodiment of an external fixation device surrounding a person's bone with a fracture.

FIG. 8D illustrates another example embodiment of an external fixation device 80000 surrounding a person's bone with a fracture. FIG. 8E illustrates a close up view the external fixation device 80000 surrounding a person's bone with a fracture. In addition to the components depicted in FIG. 8B and FIG. 8C, the example embodiments of FIG. 8D and FIG. 8E may further comprise a plurality of external fixation rods 80060, wherein each of the external fixation rods 80060 are secured at one end to an external fixation strut 8000 and at another end of one of the first external fixation ring 80020 or the second external fixation ring 80040. As described above, external fixation rods 80060 may be that of the external fixation connection rod described in U.S. Pat. No. 8,574,232, entitled External Fixation Connection Rod for Rapid and Gradual Adjustment, the disclosure of which is incorporated by reference in its entirety. Use of the external fixation connection rod described therein as external fixation rod 80060 may advantageously provide for a greater length between the first external fixation ring 80020 and the second external fixation ring 80040. Further, use of the external fixation connection rod described therein as external fixation rod 80060 may provide for greater ease in assembling the external fixation device on a patient, or adjusting the external fixation device once secured on a patient.

As explained above, the use of the disclosure in U.S. Pat. No. 8,574,232 as the external fixation rod 80060 is provided by way of example only. One of ordinary skill in the art having the benefit of the present disclosure would appreciate that an external fixation rod 80060 may comprise more or less features than that disclosed in U.S. Pat. No. 8,574,232. For example, in some embodiments, providing for various rotating members or articulatable joints in an external fixation rod 80060 may advantageously allow for greater manipulation and/or adjustment of the external fixation device 80000 and the components therein. In other embodiments, utilizing an external fixation rod 80060 with fewer articulatable joints or rotating members may advantageously maintain parallel orientation of the first external fixation ring 80020 and the second external fixation ring 80040. Further, utilizing an external fixation rod 80060 with fewer articulatable joints or rotating members may advantageously stabilize or maintain the direction or axis of dynamization provided by the external fixation struts 8000.

As seen from the above description, the present disclosure provides for various embodiments of external fixation struts. Embodiments of the present disclosure may provide for compression of a biasing member disposed within the external fixation strut. Compression of the biasing member may occur without a corresponding change in the position or movement of the shaft and/or the sleeve. Consequently, a total length of the strut may not change during adjustment. Rather, only the biasing force and potential range of motion change may be adjusted. The range of motion afforded by the external fixation strut may be effected by the biasing force, but may be mechanically limited by the position of the bushing or rotatable feature. Thus, a biasing member may be compressed without a corresponding change in the total length of the strut. Rather, any change in the length of the strut may occur as a result of external compressive forces acting upon it.

As will be understood by those skilled in the art who have the benefit of the instant disclosure, other equivalent or alternative compositions, devices, methods, and systems for external fixation struts can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated. Persons skilled in the art may make various changes in methods of preparing and using a device, and/or system of the disclosure.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints.

All or a portion of a device and/or system for external fixation struts may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the appended claims.

The title, abstract, background, and headings are provided in compliance with regulations and/or for the convenience of the reader. They include no admissions as to the scope and content of prior art and no limitations applicable to all disclosed embodiments.

The invention claimed is:

1. A dynamization strut, the strut comprising:
a sleeve, wherein the sleeve comprises:
an inner recess comprising a first section and a second section, wherein a diameter of the first section is larger than a diameter of the second section;
a shaft, wherein the shaft comprises:
an interior section configured to be disposed at least partially within the inner recess of the sleeve, and wherein the interior section comprises an annular protrusion; and
a threaded section;
a contact feature, wherein the contact feature is configured to be disposed within the inner recess of the sleeve, and wherein the contact feature comprises an annular protrusion and a longitudinal segment;
a biasing member, wherein the biasing member is configured to be disposed within the inner recess of the sleeve, and wherein the biasing member is configured to be disposed between the annular protrusion of the contact feature and the annular protrusion of the shaft; and
a rotatable feature,
wherein the rotatable feature comprises a plurality of surfaces;
wherein rotation of the rotatable feature results in a different one of the plurality of surfaces contacting the annular protrusion of the contact feature; and
wherein rotation of the rotatable feature provides for compressive movement of the biasing member relative to the sleeve and shaft.

2. The dynamization strut of claim 1, wherein the plurality of surfaces of the rotatable feature comprises four flat surfaces.

3. The dynamization strut of claim 2, wherein each of the four flat surfaces has a different distance from a center of the rotatable feature.

4. The dynamization strut of claim 3, wherein the different distances from the center of the rotatable feature comprises 3.35 mm, 4.35 mm, and 5.35 mm.

5. The dynamization strut of claim 1, wherein rotation of the rotatable feature results in compression or expansion of a spring within the inner recess of the sleeve.

6. The dynamization strut of claim 1, wherein rotation of the rotatable feature results in movement of the contact feature within the inner recess of the sleeve.

7. The dynamization strut of claim 1, wherein the sleeve further comprises a plurality of internal threads disposed at one end of the sleeve, and wherein the plurality of internal threads of the sleeve are configured to secure to an external fixation device.

8. The dynamization strut of claim 1, wherein the biasing member is a spring.

9. The dynamization strut of claim 8, wherein the spring has a spring constant of about 3.50 pounds/mm to about 4 pounds/mm.

10. The dynamization strut of claim 8, wherein the longitudinal segment of the contact feature is in contact with the annular protrusion of the shaft when the spring is fully compressed.

11. The dynamization strut of claim 1, wherein the sleeve has a length of about 35 mm to about 50 mm, and wherein the shaft has a length of about 30 mm to about 45 mm.

12. The dynamization strut of claim 1, the dynamization strut further comprising an interior component, wherein the interior component is configured to be disposed within the first section of the sleeve.

13. The dynamization strut of claim 12, wherein an end of the first section of the sleeve comprises a narrowed section, and wherein the narrowed section is in contact with the interior component and secures the interior component within the first section of the sleeve.

* * * * *